United States Patent
Dalton et al.

(10) Patent No.: US 11,031,122 B1
(45) Date of Patent: Jun. 8, 2021

(54) METHODS, SYSTEMS, AND APPARATUS FOR IMPROVING OPERATING ROOM THROUGHPUT

(71) Applicant: Pelorus Systems, LLC, Wilmington, NC (US)

(72) Inventors: Thomas Maxwell Dalton, Wilmington, NC (US); John A. Philips, III, Wilmington, NC (US)

( * ) Notice: Subject to any disclaimer, the term of this patent is extended or adjusted under 35 U.S.C. 154(b) by 1158 days.

(21) Appl. No.: 15/398,707

(22) Filed: Jan. 4, 2017

Related U.S. Application Data

(60) Provisional application No. 62/274,776, filed on Jan. 4, 2016, provisional application No. 62/289,912, filed on Feb. 1, 2016.

(51) Int. Cl.
*G16H 40/20* (2018.01)
*G06F 19/00* (2018.01)
*G16H 10/60* (2018.01)

(52) U.S. Cl.
CPC .......... *G16H 40/20* (2018.01); *G06F 19/321* (2013.01); *G16H 10/60* (2018.01)

(58) Field of Classification Search
CPC ....... G16H 40/20; G16H 10/60; G06F 19/321
USPC ...................................................... 705/2–3
See application file for complete search history.

(56) References Cited

U.S. PATENT DOCUMENTS

| | | | | |
|---|---|---|---|---|
| 2006/0053034 A1* | 3/2006 | Hlathein | ............... | G16H 40/20 705/2 |
| 2013/0054260 A1* | 2/2013 | Evans | .................... | G06Q 10/06 705/2 |
| 2013/0304499 A1* | 11/2013 | Rangadass | ..... | G06Q 10/063114 705/2 |
| 2014/0039906 A1* | 2/2014 | Wang | .................... | G06Q 10/06 705/2 |
| 2014/0067413 A1* | 3/2014 | Ghivizzani | ........... | G16H 40/20 705/2 |

OTHER PUBLICATIONS

Agnoletti, V., Buccioli, M., Padovani, E. et al. Operating room data management: improving efficiency and safety in a surgical block. BMC Surgery 13, 7 (2013). https://doi.org/10.1186/1471-2482-13-7 http://www.biomedcentral.com/1471-2482/13/7 (Year: 2013).*

(Continued)

*Primary Examiner* — Joy Chng
(74) *Attorney, Agent, or Firm* — Chad D Tillman; Tillman Wright, PLLC

(57) ABSTRACT

Apparatus, systems, and methods relate to one or more operating rooms; one or more display screens located in the one or more operating rooms; one or more display screens located outside of the one or more operating rooms; and a computer apparatus comprising computer hardware and software, which is operatively connected to an EMR system and is configured so as to receive from the EMR system utilization information regarding the one or more operating rooms. The computer apparatus is further configured to cause to be displayed one or more generated graphics or graphical user interfaces (GUIs) showing operating room efficiency information, in real time, for view on the one or more display screens in the one or more operating rooms, and on the one or more display screens located outside of the one or more operating rooms.

17 Claims, 20 Drawing Sheets

(56) References Cited

OTHER PUBLICATIONS

Fixler, T., & Wright, J. G. (2013). Identification and use of operating room efficiency indicators: the problem of definition. Canadian journal of surgery. Journal canadien de chirurgie, 56(4), 224-226. https://doi.org/10.1503/cjs.020712 (Year: 2013).*

J. Sutherland and W. van den Heuvel, "Towards an Intelligent Hospital Environment: Adaptive Workflow in the OR of the Future," Proceedings of the 39th Annual Hawaii International Conference on System Sciences (HICSS'06), Kauia, HI, USA, 2006, pp. 100b-100b, doi: 10.1109/HICSS.2006.494. (Year: 2006).*

\* cited by examiner

FIG. 16

METHODS, SYSTEMS, AND APPARATUS FOR IMPROVING OPERATING ROOM THROUGHPUT

CROSS-REFERENCE TO RELATED APPLICATION

The present application is a nonprovisional patent application of, and claims priority under 35 U.S.C. § 119(e) to, each of U.S. provisional patent application 62/274,776, filed Jan. 4, 2016, and incorporated by reference herein; and, U.S. provisional patent application 62/289,912, filed Feb. 1, 2016, and incorporated by reference herein. The disclosure of the '776 provisional application is contained in the Appendix included herewith, which is incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to efficiencies in use of operating rooms when providing healthcare services to patients and, in particular, to technological innovations including methods, systems, and apparatus that improve operating room throughput in the operating rooms of a healthcare facility—such as a hospital, or of a healthcare system—such as multiple associated hospitals.

Operating rooms are one of the most expensive places in the world, and patients have become more impatient when waiting for medical services. Despite an immense effort to computerize the hospital experience through electronic medical record systems (EMRs), which also are referred to as electronic healthcare record systems (EHRs), improving operating room throughput remains an elusive challenge for health care providers. Indeed, most administrators and surgeons at hospitals/healthcare facilities/healthcare systems in the United States have regular discussions about prolonged operating room "turnover time", which is a term defined as the time interval from when one patient leaves the operating room to when the next patient arrives in the operating room, commonly documented in the EMR as "patient out" to "patient in".

Even in view of the foregoing, efficient OR throughput remains an elusive goal for many hospitals to maximize. Operating rooms (ORs) are the main financial generators for hospitals, and large resources are consumed in tracking and improving OR efficiency metrics. Consultants are often hired to look for process opportunities, improving patient flow and patient experience. Institutional variation regarding data definitions also is a problem, especially for widespread use of EMRs. For example, it is important to start the ORs on time, but many hospitals consider the patient's arrival to the operating room as the start, while others track the incision time as the start.

Moreover, while hospital EMRs are being implemented in widespread fashion in ORs, and most physicians, nurses, and hospital administrators have come to recognize that EMRs are an excellent data collection apparatus, such persons remain frustrated by user interfaces currently provided by such EMRs. It is difficult to quickly find important data amidst all of the detailed documentation. The reporting mechanisms within the EMR are particularly difficult to negotiate, and EMR-related OR display boards are often too busy to quickly find information.

In view of the foregoing, and even in view of the implementation and utilization of EMRs, one or more needs are believed to exist for further improvement in increasing efficiencies in OR throughput. One or more such needs are believed to be addressed by one or more aspects and features of the invention. Indeed, in one or more preferred embodiments, EMR data is used to display information in a simple and effective fashion so as to improve OR throughput without increasing data entry workload of staff.

BRIEF SUMMARY OF THE INVENTION

The invention includes many aspects and features.

In an aspect of the invention, an apparatus for improving operating room throughput for a plurality of operating rooms of a healthcare facility/healthcare system includes: (a) a networked data collector module comprising a networked electronic device having a processor and computer-executable instructions by which the networked data collector module is configured to receive data in real-time indicating a patient's arrival in an operating room and the patient's departure from the operating room and, based thereon, populate data in a database; (b) a networked display manager module comprising computer-executable instructions by which the networked display manager module is configured to analyze data in the database populated by the data collector module and calculate data for display including real-time first case on time start (FCOTS) metrics, real-time operating room utilization metrics, and operating room turnover time metrics; and (c) a plurality of networked display modules, each networked display module comprising a networked electronic device having a processor and computer-executable instructions by which the networked display module is configured to receive and display data calculated by the networked display manager module including at least one of the real-time FCOTS metrics, the real-time operating room utilization metrics, and the operating room turnover time metrics.

In a feature, the networked electronic device comprises a networked electronic device having a processor.

In another aspect, a system for improving operating room throughput for a plurality of operating rooms of a healthcare facility/healthcare system includes: (a) a networked data collector module comprising a networked electronic device having a processor and computer-executable instructions by which the networked data collector module is configured to receive data indicating a patient's arrival in an operating room and the patient's departure from the operating room and, based thereon, populate data in a database; (b) a networked display manager module comprising a networked electronic device having a processor and computer-executable instructions by which the networked display manager module is configured to analyze data in the database populated by the data collector module and calculate data for display including real-time first case on time start (FCOTS) metrics, real-time operating room utilization metrics, and operating room turnover time metrics; and (c) a plurality of networked display modules, each networked display module comprising a networked electronic device having a processor and computer-executable instructions by which the networked display module is configured to receive and display data calculated by the networked display manager module including at least one of the real-time FCOTS metrics, the real-time operating room utilization metrics, and the operating room turnover time metrics; (d) wherein each of the plurality of operating rooms of the healthcare facility has located therein a display by which operating room personnel may view a display generated by one of the plurality of networked display modules, the generated display including at least one of the real-time FCOTS metrics, the real-time operating room utilization metrics, and the operating room turnover time metrics.

In a feature, the healthcare facility comprises a hospital.

In a feature, the plurality of operating rooms comprises all of the operating rooms of the healthcare facility.

In a feature, the healthcare system comprises a plurality of healthcare facilities.

In a feature, the plurality of operating rooms comprises all of the operating rooms of the healthcare system.

In a feature, the FCOTS metrics are expressed as percentages representing the number of cases scheduled to start in the operating rooms at a specified time or within a specified window of time that did, in fact, start at or before such specified time.

In a feature, the database includes scheduling information for each of the plurality of operating rooms for calculating the FCOTS metrics.

In a feature, the real-time operating room utilization metrics are calculated every minute.

In a feature, the networked display module is further configured to display color-coded time clocks identifying delayed operating room start times and unacceptable operating room turnover times.

In a feature, the networked data collector module receives data relating to clinical metrics and populates the database based thereon, and wherein the networked display module is further configured to display data from the database relating to the clinical metrics. The data relating to the clinical metrics may comprise data regarding antibiotics; data regarding antibiotic timing or antibiotic dosing; data regarding a patient temperature; data regarding patient blood glucose level; data regarding beta blockers; and combinations of such data.

In a feature, the networked electronic device of the networked data collector module comprises a server that communicates with a computer network of the healthcare facility.

In further to this regard, an HL7 feed may be used to communicate between the data collector module and the computer network of the healthcare facility; the communication may comprise a one-way data feed from the computer network of the healthcare facility to the server; and the communication may be over the Internet. The data collector module also may obtain data from the EMR system of the computer network of the healthcare facility, which data that is obtained is EMR data that is already being recorded for a patient for other purposes, whereby the system leverages the patient EMR data for an additional purpose. Furthermore, the data collector module may collect information from computer network of the healthcare facility and populate a database with the collected information, and the server may be located in a data center. The data center may be located on premises of the healthcare facility or located off premises with respect to the healthcare facility, and the server may be owned, operated, or maintained by the healthcare facility or by a third party that is unrelated to the healthcare facility, which third party is a service provider to the healthcare facility. Preferably, the networked electronic device of the display manager module comprises a server that communicates with a computer network of the healthcare facility.

In another feature, the networked display manager module is configured to provide a data feed of the calculated data for receipt by the plurality of networked display modules.

In another feature, an employee-only area of the healthcare facility outside of the plurality of operating rooms has located therein a display by which personnel of the healthcare facility may view a display generated by one of the plurality of networked display modules. The employee-only area may be a surgeon lounge, or a key common area that is accessible to healthcare providers but, preferably, not the public.

In another feature, the display includes a room utilization summary for the plurality of the operating rooms of the healthcare facility.

In another feature, a room utilization summary is displayed in an employee-only area that shows a mini-display of each display that is concurrently being displayed in each of the plurality of operating rooms.

In another feature, the generated display includes at least one of real-time FCOTS metrics, real-time operating room utilization metrics, and operating room turnover time metrics.

In another feature, the system further comprises a surgeon sign-in module comprising a networked electronic device having a processor and computer-executable instructions, by which the surgeon sign-in module is configured to receive user input indicating that a surgeon is ready to begin a case of that surgeon in a specific operating room, and by which the networked electronic device is configured to communicate data indicative that the surgeon is ready for storing such data in the database populated by the networked data collector module. Preferably, the networked electronic device comprises a tablet computer located in a preoperative area of the healthcare facility.

Further in this regard, the networked display manager module is configured to provide data, indicative that the surgeon is ready to perform a procedure, to a networked display module for display in the specific operating room in which the surgeon is ready to perform the procedure. The indication that the surgeon is ready that is displayed in the specific operating room preferably includes the time at which the user input was received indicating that the surgeon was ready to begin the case in the specific operating room.

The networked display module further preferably is configured to display indicators that show when a surgeon is concurrently using two operating rooms, and preferably showing when a surgeon is concurrently using two operating rooms with acceptable downtimes; the indicators preferably comprise hashed patterns.

In another aspect, a computer apparatus includes computer hardware and software and receives a one-way data feed from an EMR system for a patient currently in an operating room on whom a surgeon is performing a procedure and displays, in real time, visual indications of operating room efficiency information pertaining to such use of the operating room for performing the procedure on the patient. The displayed information preferably includes, for example and not by way of limitation: an identification of the specific operating room as compared to other operating rooms; an identification of the surgeon as compared to other surgeons; an identification of the patient as opposed to other patients; a running counter showing the running time, i.e., interval, of the procedure; and the immediately prior turnover time of the operating room. The information preferably is displayed in such manner and locations so as to be seen by healthcare providers in the operating room and by other healthcare providers and healthcare administrators outside of the operating room. The information preferably is not displayed in such manner and locations so as to be publicly viewable.

In another aspect of the invention, a system includes: one or more operating rooms of a healthcare facility; one or more display screens located in the one or more operating rooms, with at least one of the one or more display screens being located in each of the one or more operating rooms at the healthcare facility; one or more display screens located outside of the one or more operating rooms at the healthcare facility; and a computer apparatus—including computer hardware and software—that is configured and operatively connected to an EMR system of the healthcare facility so as to receive, via a one-way data feed from the EMR system, utilization information regarding the one or more operating rooms, and that is configured to cause to be displayed one or more generated graphics showing operating room efficiency information, in real time, for view both by healthcare providers on the one or more display screens in the one or more operating rooms at the healthcare facility, and by other healthcare providers and healthcare administrators on the one or more display screens located outside of the one or more operating rooms at the healthcare facility.

In features, the display screens comprise touchscreens, by which user input may be received; and, the displayed one or more generated graphics showing operating room efficiency information comprise one or more graphical user interfaces (GUIs).

In another aspect, a system comprises an operating room, a display screen located in the operating room, a display screen located outside of the operating room, and computer apparatus including computer hardware and software, wherein the computer apparatus receives a one-way data feed from an EMR system for a patient currently in a hospital operating room and displays in real time clinical and operating room efficiency information both to healthcare providers on the display in the operating room at the healthcare facility, and to other healthcare providers and healthcare administrators on the display screen outside of the operating room at the healthcare facility. The display of such information may be by the display of one or more generated graphics; and, the displayed one or more generated graphics showing such information may comprise one or more graphical user interfaces (GUIs).

In another aspect, a system includes: one or more operating rooms; one or more display screens located in the one or more operating rooms, with each of the one or more operating rooms having at least one of the one or more display screens located therein; one or more display screens located outside of the one or more operating rooms; and a computer apparatus comprising computer hardware and software, which computer apparatus is operatively connected to an EMR system and is configured so as to receive from the EMR system, via a one-way data feed from the EMR system, utilization information regarding the one or more operating rooms, and which computer apparatus is configured to cause to be displayed one or more graphical user interfaces (GUIs) showing operating room efficiency information, in real time, for view both by healthcare providers on the one or more display screens in the one or more operating rooms at the healthcare facility, and by other healthcare providers and healthcare administrators on the one or more display screens located outside of the one or more operating rooms at the healthcare facility.

In a feature, the one or more operating rooms comprise operating rooms located at a healthcare facility. Additionally, the computer apparatus may comprise a server located at the healthcare facility or located remotely to the healthcare facility.

In a feature, the one or more operating rooms comprise operating rooms located at a plurality of healthcare facilities. The healthcare facilities may constitute a healthcare system. Additionally, the computer apparatus may comprise a server located at one of the healthcare facilities or located remotely to all of the healthcare facilities.

In additional features of this aspect, one or more of the aforementioned healthcare facilities may comprise a hospital.

In a feature of this aspect, the one or more display screens comprise one or more monitors mounted on a portable cart apparatus.

In a feature of this aspect, the one or more display screens comprise one or more wall-mounted monitors.

In a feature of this aspect, the one or more display screens comprise one or more ceiling-mounted monitors.

In a feature of this aspect, the utilization information comprises operating room efficiency information.

In a feature, the utilization information comprises indicators that show when a surgeon is concurrently using two operating rooms. The indicators may comprise hashed patterns.

In a feature, the utilization information comprises indicators that show when a surgeon is concurrently using two operating rooms with acceptable downtimes. The indicators may comprise hashed patterns.

In a feature of this aspect, the utilization information comprises clinical and operating room efficiency information.

In another feature, the utilization information comprises "First Case On Time Starts" data for one or more of the operating rooms for the day.

In another feature, the computer apparatus is configured to automatically turn on and display, for each day, a countdown clock on each display screen in each operating room having a scheduled case that day. The display of the countdown that is turned preferably occurs at a predetermined time interval preceding the scheduled start time for each operating room. Preferably, the predetermined time interval represents forty-five minutes prior to the time a patient is scheduled to be in an operating room.

In additional features, the computer apparatus is operatively connected to an EMR system and is configured so as to receive from the EMR system the utilization information regarding the one or more operating rooms via a one-way data feed from the EMR system. Furthermore, in such a configuration the computer apparatus may be maintained by a third party service provider to the healthcare facility or hospital, wherein the one-way data feed preferably precludes alteration, addition, or deletion of data from the EMR system by the computer apparatus.

In additional aspects of the invention, a method for improving operating room throughput is performed by apparatus and systems of the foregoing aspects.

In accordance with one or more preferred embodiments of the invention, a visual management based computer system (sometimes referred to herein as the "Pelorus" system) is designed to use data that is already collected by hospitals and display it in a fashion that improves workflow. Dedicated 46-inch computer displays are positioned in each operating room and summary displays are positioned in key common areas accessible to the healthcare providers. The displays show easy to read, color-coded time clocks to identify when work is being completed in a timely fashion and easily identifies when delays are occurring.

An aspect of one or more preferred embodiments of the invention comprises a system including a computer apparatus including a program and associated computer hardware that receives a one-way data feed from an EMR system of a hospital operating room and displays in a visually easy to comprehend fashion using innovative views of clinical and operating room efficiency-related information in real time to the healthcare providers in the operating room as well as preferably to their colleagues and healthcare administrators. Proactive visual management preferably is achieved with simple green and red blocks as well as running clocks offering real time feedback in each operating room throughout the healthcare facility or healthcare system. It is believed that such tracking and immediate performance feedback make workers more efficient, and this concept is extended to the OR in accordance with one or more aspects and features of the invention. Furthermore, current OR clinical and efficiency reporting methods often take days, weeks and months to report results with significant medical costs at risk. Preferably such aspects and features of the invention require little additional user input outside of that which is already performed in association with the EMR.

In addition to the aforementioned aspects and features, it should be noted that the present invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the present invention now will be described in detail with reference to the accompanying drawings, wherein the same elements are referred to with the same reference numerals.

FIG. 16 illustrates a computer generated graphic as would be seen on a display screen of a display screen located outside of an operating room, which includes display of an exemplary utilization screen comprising an operating room summary screen, in accordance with one or more aspects and features of a preferred embodiment.

DETAILED DESCRIPTION

Figure 1:
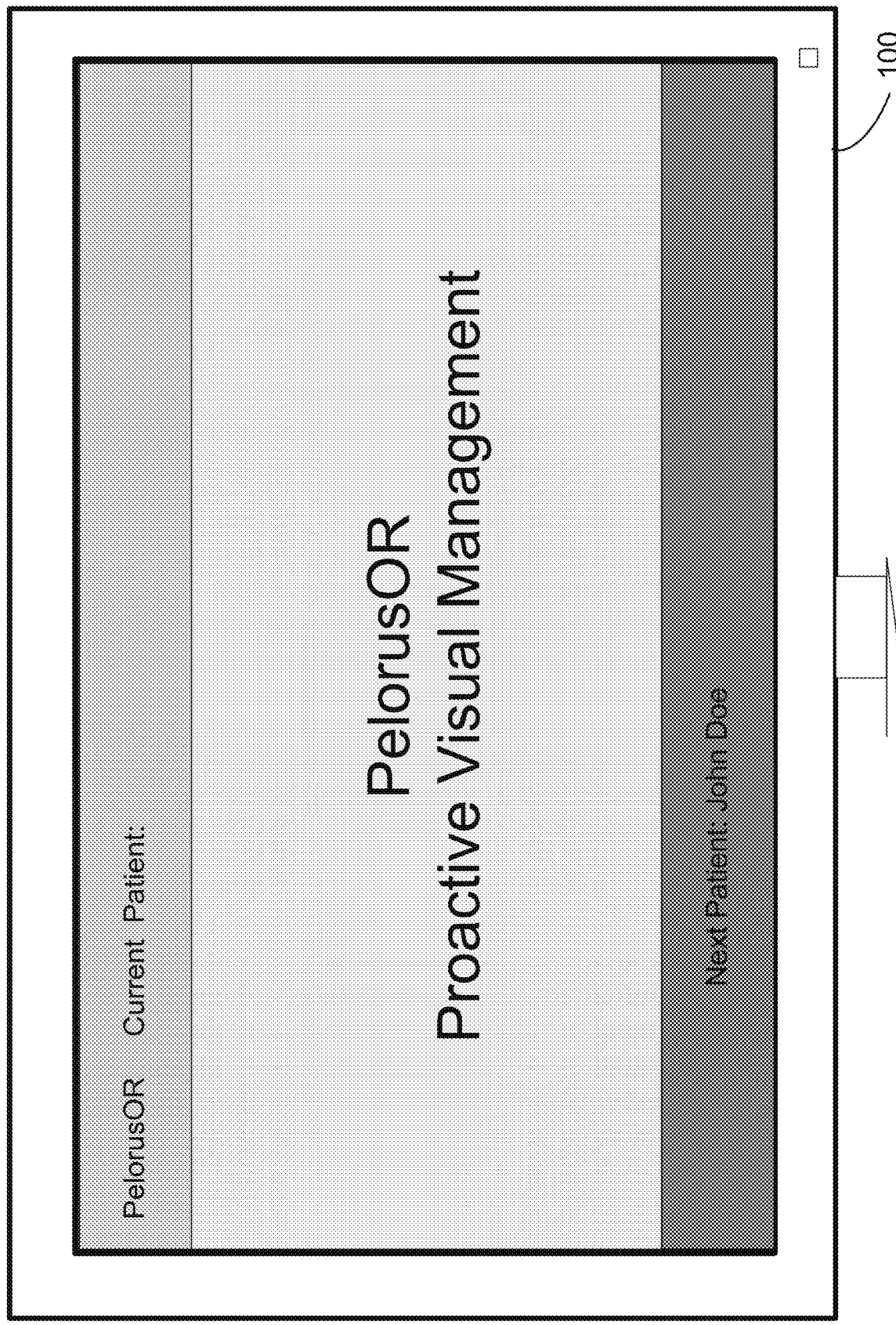
FIG. 1 illustrates a computer generated "Start-Up" graphic as would be initially seen on a display screen in an operating room, such as a "flight board" or other electronic display device, in accordance with one or more aspects and features of a preferred embodiment.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

At the beginning of a given day, the first operation of the day should start on time, but experience shows that even well-functioning operating rooms frequently start after the scheduled start time. There are three main factors in getting the first case started on time: the patient must arrive and be prepared for the operating room; the operating room must be prepared to receive the patient; and the surgeon must be available.

The Pelorus system addresses these issues by automatically starting, for each operating room, and for each day, a green countdown clock at a predetermined time period before the scheduled first case start. In at least one implementation, the predetermined time period is forty-five minutes prior to the scheduled first case start time. Thus, if the first case starts at 7:15 am, then the Pelorus system begins with a green clock that starts at 6:30 am and counts down to the first start of the day.

Figure 2:
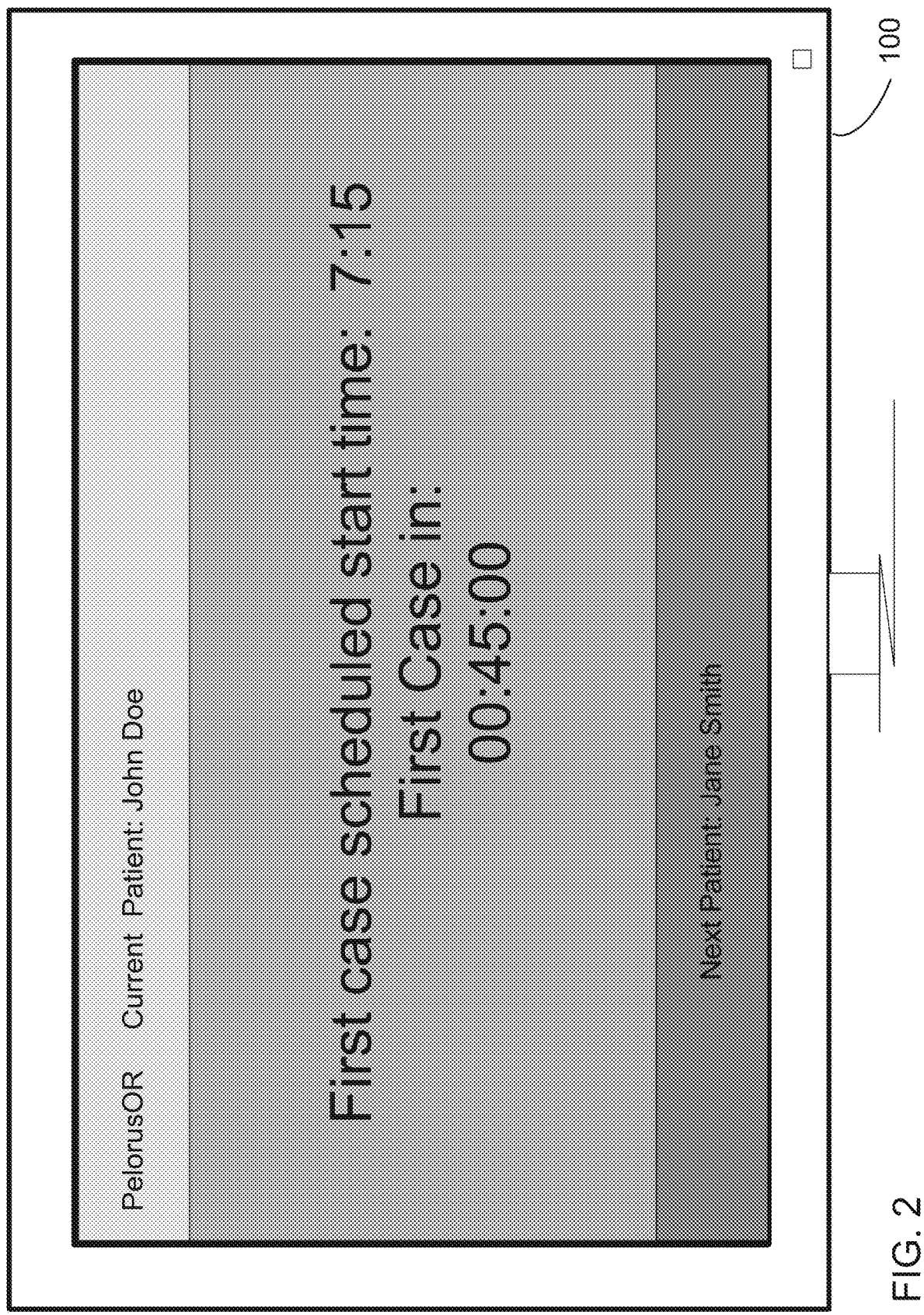
FIG. 2 illustrates a computer generated "First Case On Time Start (FCOTS) Countdown Clock" graphic as would be seen on the display screen of FIG. 1, which is automatically displayed at a predetermine time interval prior to the first case start time for a first scheduled case in the operating room.

This is represented in FIGS. 1 and 2. In this respect, FIG. 1 illustrates a "Start-Up" screen as would be initially seen on a display 100 (such as an electronic monitor, "flight board", or other electronic display device) in an operating room in accordance with one or more aspects and features of the invention. Such a display preferably is located in each operating room. FIG. 2 shows on a display screen thereof a "First Case On Time Start (FCOTS) Countdown Clock" screen on the display of FIG. 1 which is automatically turned on at the predetermine time interval prior to the first case start time. As seen in FIG. 2, the first case start time is shown to be scheduled at 7:15 am, and the first case is shown to start in 45 minutes on a countdown clock. Moreover, the countdown clock preferably is color-coded (e.g., the background of the display box of the clock is color-coded) and, in this scenario, the display of the background of the clock is green to indicate no delay has yet been experienced. The display further shows the patient for the first case in the header and the next patient scheduled in the operating room in the footer of the display screen.

Operational parameters in the Pelorus system preferably are controlled via a utilization application and preferably include the program starting at 06:30 AM when all of the OR displays turn on and beginning a 45-minute countdown to the time the patients are scheduled to be in the operating rooms. The first start time and the predetermined time interval preceding the first start time preferably can be set customized by a user according to the preferences at a healthcare facility or healthcare system.

The Pelorus system further includes a surgeon sign-in kiosk that is used at least preferably for the first case in each operating room. Accordingly, if a surgeon has a scheduled first case, then the surgeon's name is listed in alphabetical order on a touchscreen tablet awaiting for the surgeon to simply push a single button sending a message to the specific operating room that the surgeon has arrived, and thereby notifying the entire operating room personnel of the surgeon's arrival. A time stamp of the surgeon's arrival is documented as well and preferably is displayed on the flight board in the operating room in which the surgeon will be working. This is believed to encourage personnel to arrive in a timely fashion and public reporting of this information usually helps improve this factor. In hospitals, a surgeon preferably is requested to check-in fifteen minutes prior to the operating room's scheduled start time.

Figure 3:
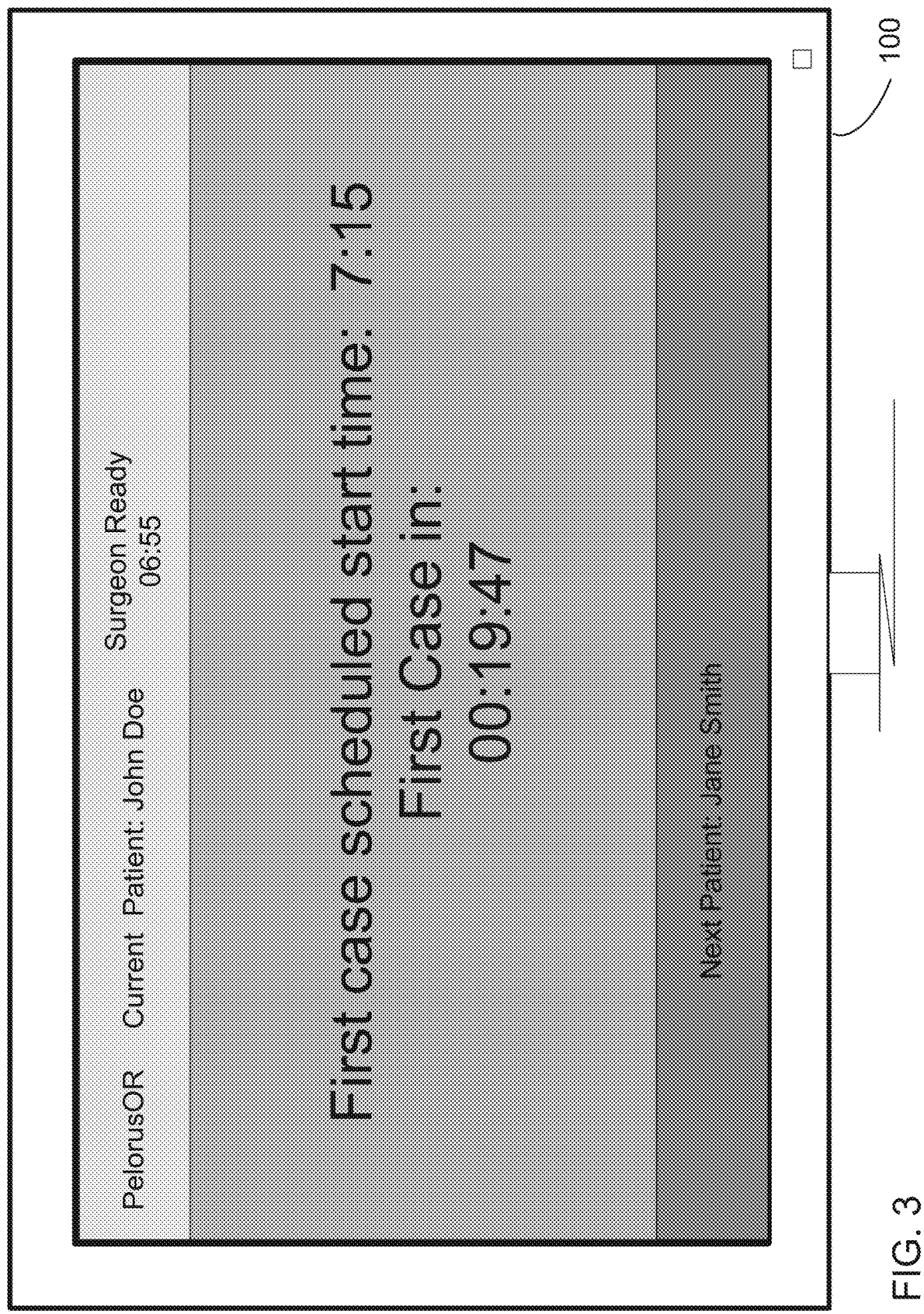
FIG. 3 illustrates a computer generated graphic as would be seen on the display screen of FIG. 1, which includes display of an indication of a surgeon's arrival and readiness to begin a case.
Figure 20:
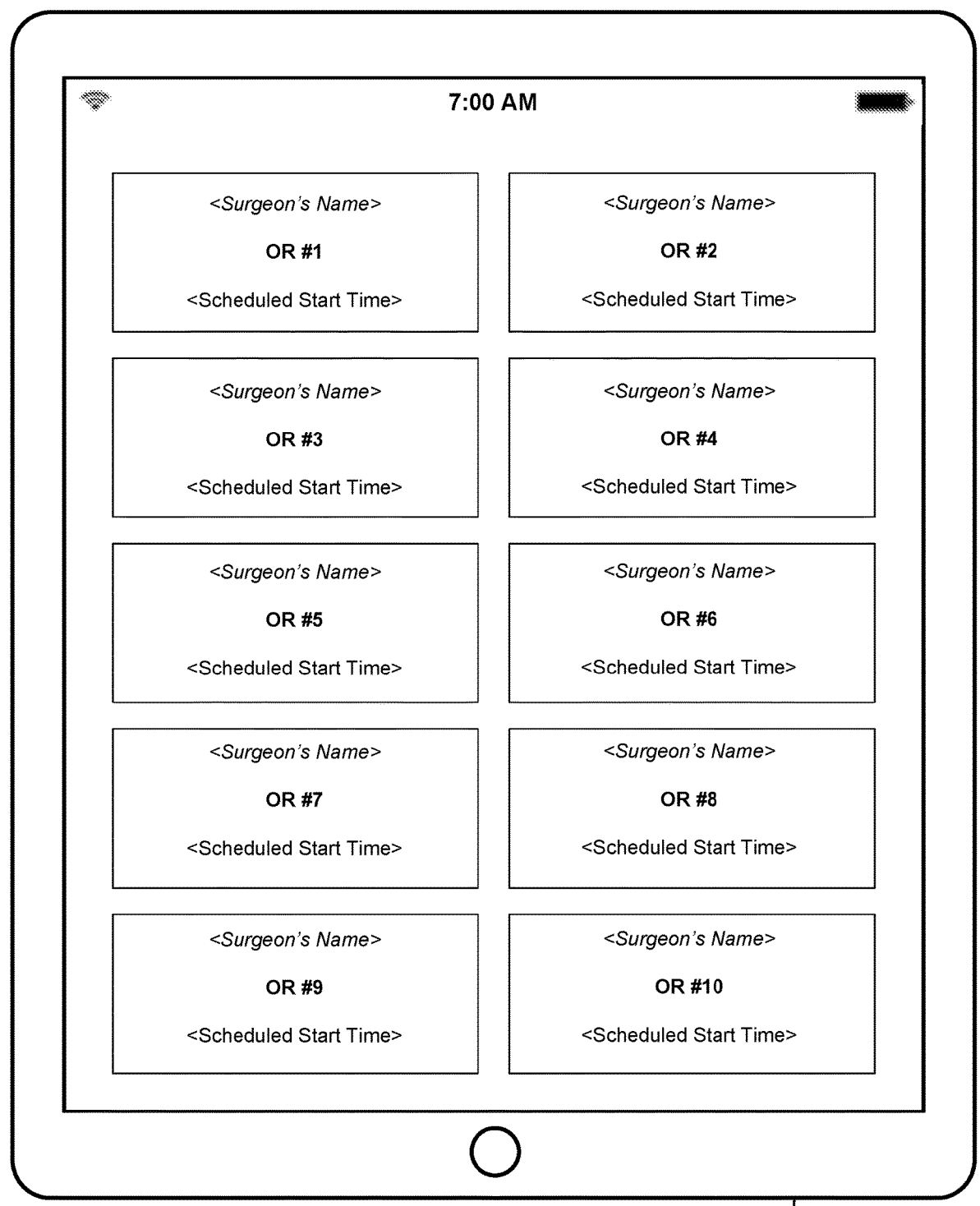
FIG. 20 illustrates a computer generated graphic as would be seen on a tablet device, which includes display of a representative graphical user interface for check-in of a surgeon, wherein each button includes an operating room designation, and the surgeon's name associated with the operating room for the next scheduled case.

The display of a surgeon's arrival and indication of readiness to begin a case is perhaps best represented in FIG. 3, wherein the display of FIG. 2 has changed to additionally display a "Surgeon Ready" indicator with the timestamp of 06:55 am—the time that the surgeon checked-in via the tablet thereby indicating the readiness of the surgeon to begin the procedure. A view of a representative graphical user interface for the touchscreen tablet 400 (such as an iPad) is seen in FIG. 20, wherein each button includes the operating room designation and the surgeon's name.

Figure 4:
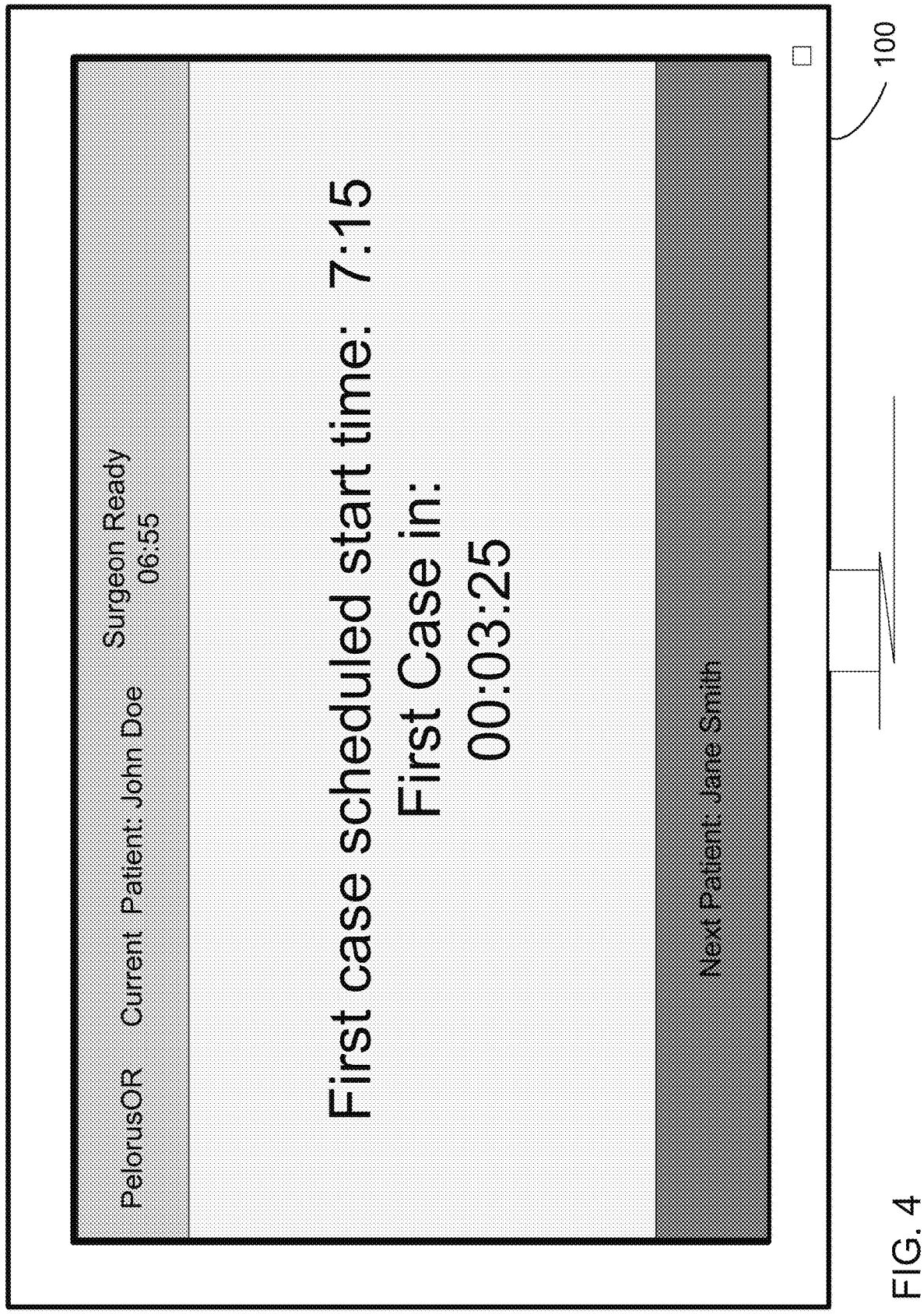
FIG. 4 illustrates a computer generated graphic as would be seen on the display screen of FIG. 1, which includes display of an indication of a warning of a possible delay in the scheduled start of a case.

Referring now to FIG. 4, if a patient is not in an operating room within a predetermined time interval (e.g., five minutes before the start time, such as by 07:10 am in the illustrated example), then the display preferably turns yellow as a warning of a possible delay in the start of the case. This is perhaps best illustrated in FIG. 4, wherein the display of FIG. 3 has changed from green to yellow and the countdown clock to the first start time of 07:15 am shows only three minutes and twenty-five seconds remaining for an on-time start of the first case.

Figure 5:
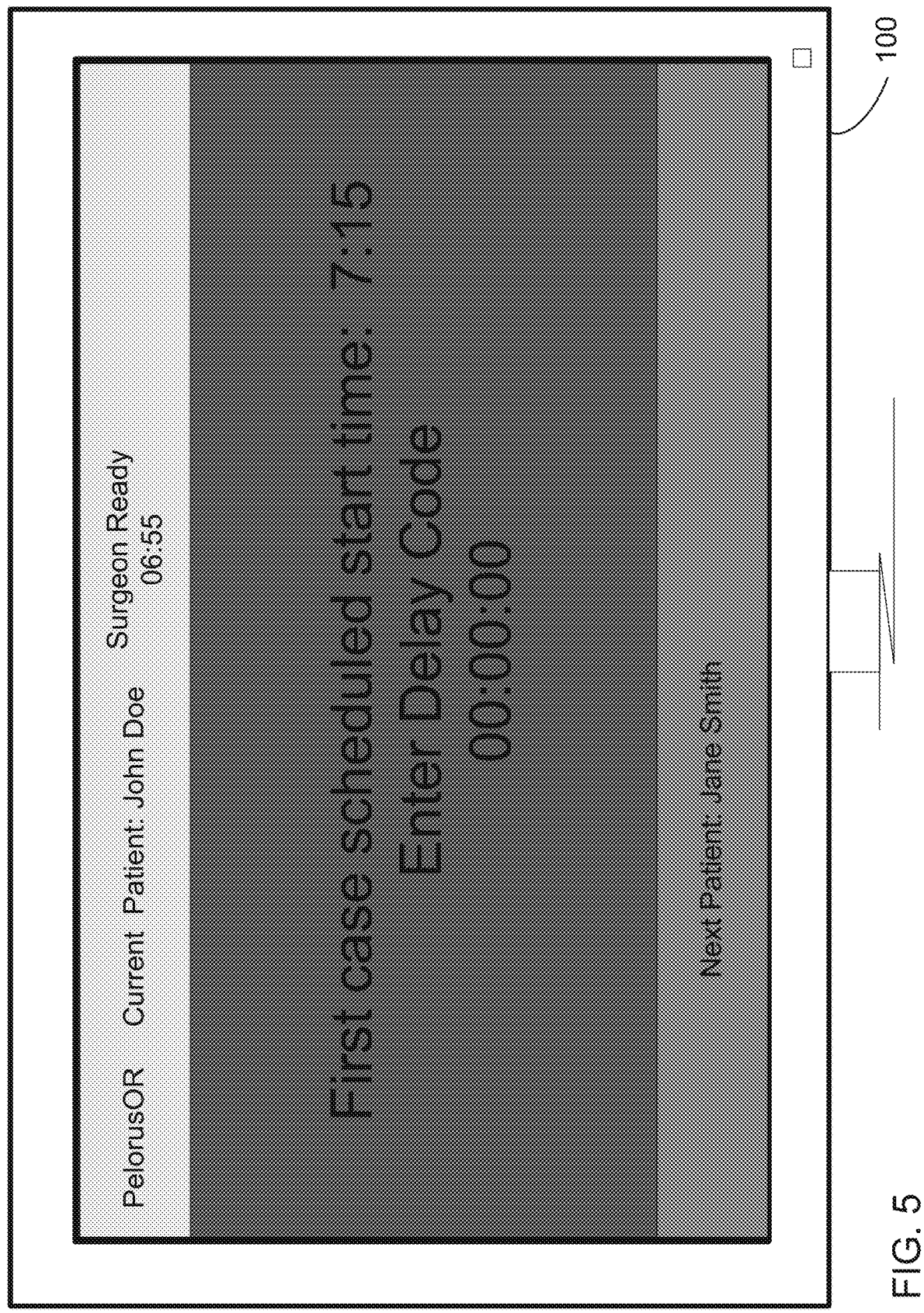
FIG. 5 illustrates a computer generated graphic as would be seen on the display screen of FIG. 1, which includes display of an indication of a requirement to enter a delay code due to a late starting of a scheduled case.

If the patient is not in the operating room by 07:15 am, then the board turns red and additionally then reads "Enter Delay Code" to prompt a circulating nurse to enter a delay code into the computer system. This is illustrated in FIG. 5, wherein the display of FIG. 4 has turned red and "Enter Delay Code" now is shown. It is noted that delay codes are now standardized and it is believed that visual awareness through the Pelorus system of the scheduled start time will result in changes to staff behavior.

Figure 6:
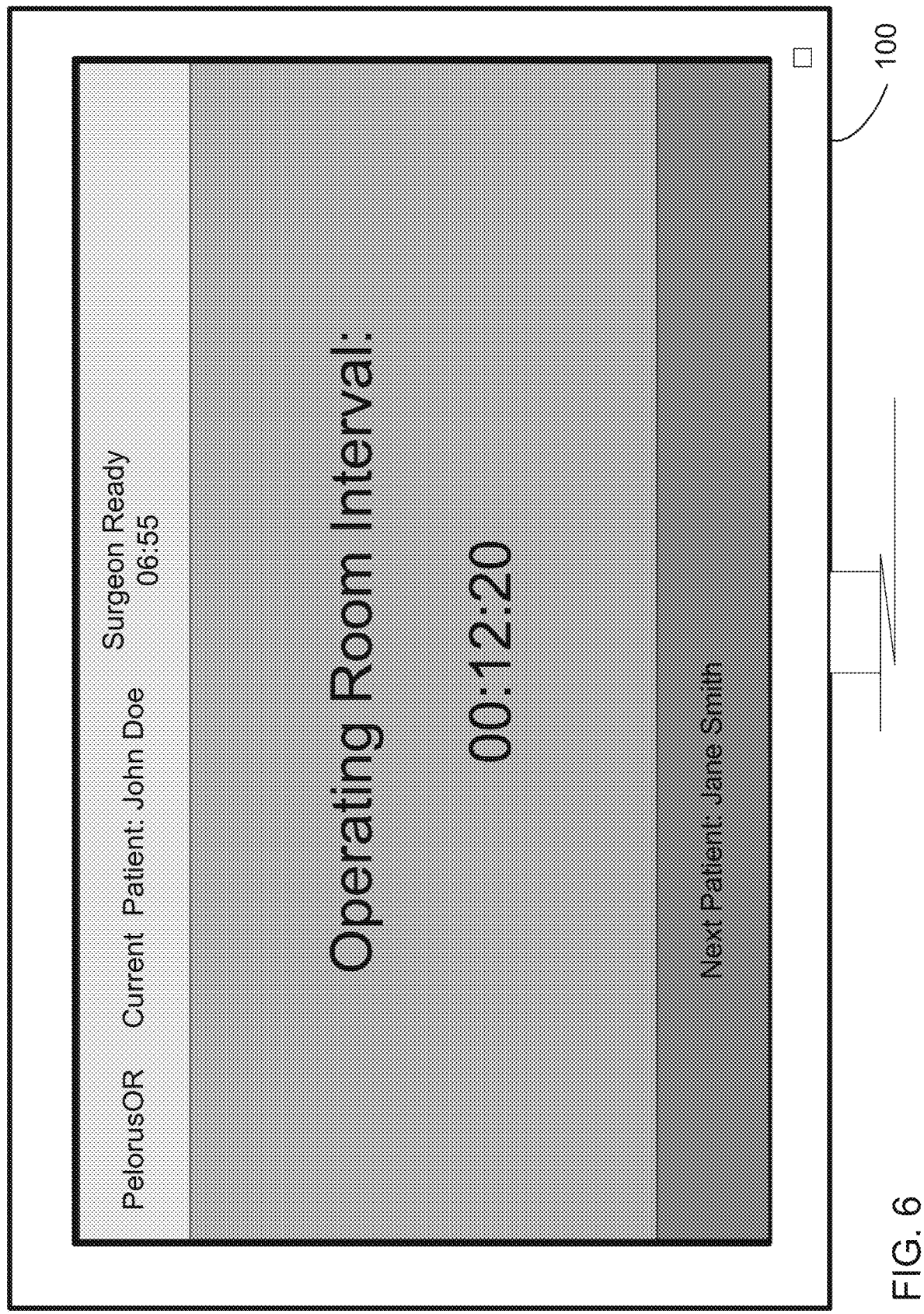
FIG. 6 illustrates a computer generated graphic as would be seen on the display screen of FIG. 1, which includes display of an indication of an operating room interval time clock that has begun for a scheduled case.

When a patient is documented as in the operating room, an operating room interval time clock begins, which signifies the start of the case. Getting the "first case on time start" (FCOTS) correct typically sets the efficiency tone for the entire day and therefore can be important. In particular, once a patient is received in the room, the arrival of the patient is recorded in the patient's EMR and the Pelorus system begins the display of a procedure interval clock as seen, for example, in FIG. 6, wherein the clock indicates that the procedure has taken twelve minutes and twenty seconds so far. Moreover, the procedure interval clock in FIG. 6 is shown in green to indicate that the time interval for the procedure currently has taken an acceptable length of time.

Figure 7:
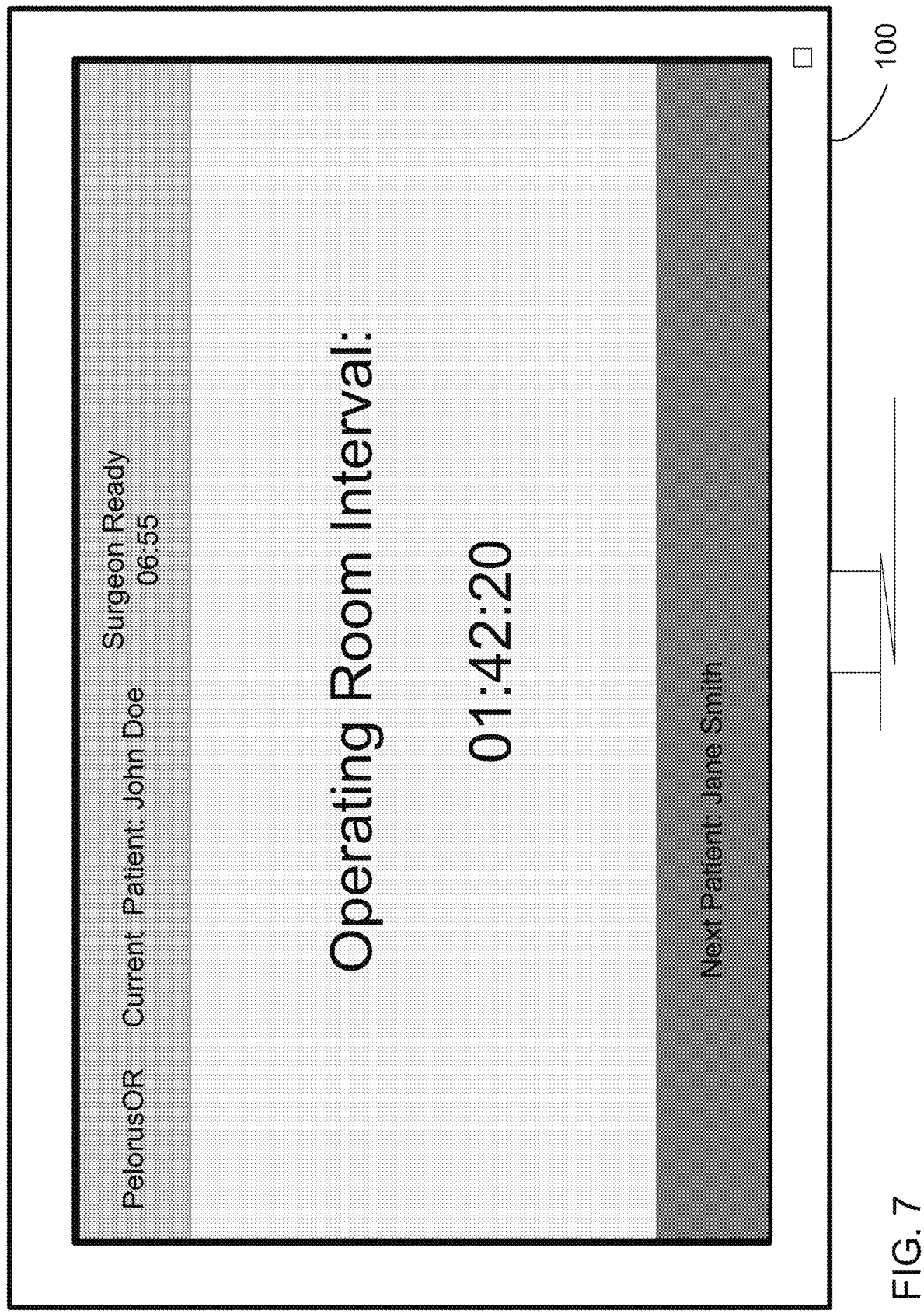
FIG. 7 illustrates a computer generated graphic as would be seen on the display screen of FIG. 1, which includes display of an indication that a scheduled case is taking longer than normal.
Figure 8:
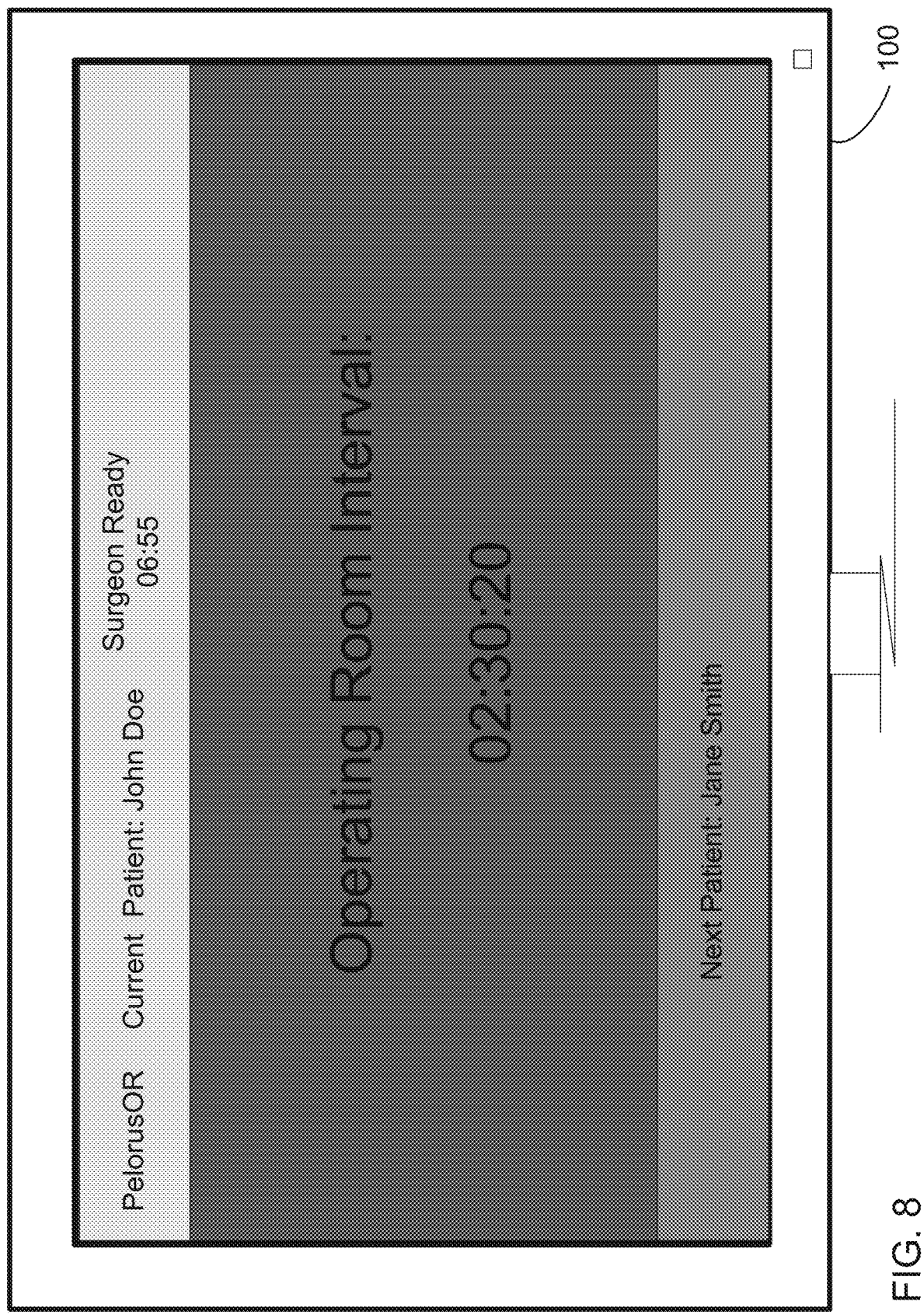
FIG. 8 illustrates a computer generated graphic as would be seen on the display screen of FIG. 1, which includes display of an indication that a scheduled case is taking longer than acceptable.

Depending on the procedure, a predetermined time interval can be set, after which the procedure interval clock turns yellow (as seen for example in FIG. 7) to indicate that the procedure is taking longer than normal, or turns red (as seen for example in FIG. 8) to indicate that the procedure is taking an unacceptable period of time. Alternatively, the procedural interval clock can remain green during the procedure to avoid undue pressure being placed on the surgeon or otherwise distracting the surgeon; the length of the procedure itself can be analyzed and discussed afterwards if desired.

Figure 9:
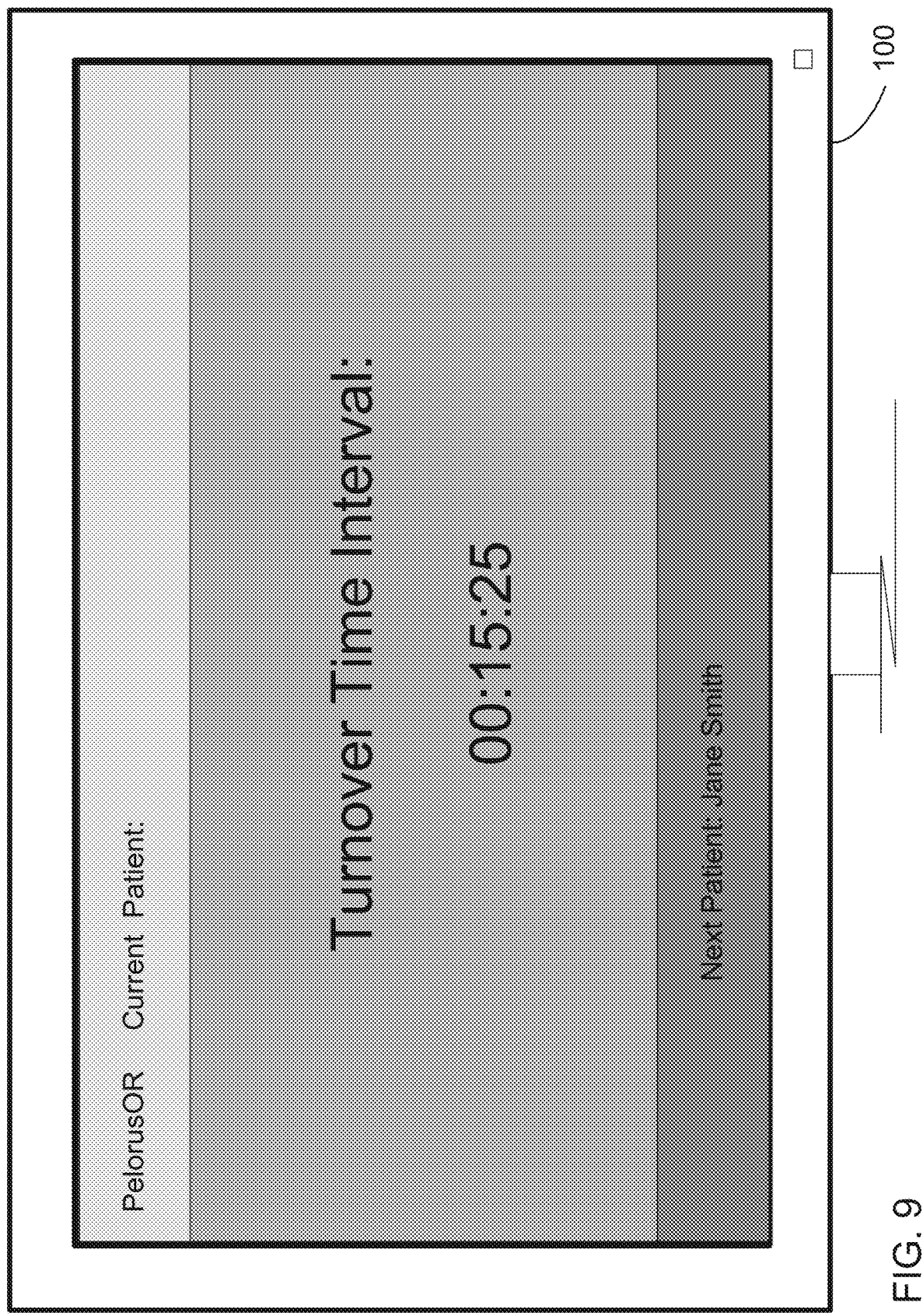
FIG. 9 illustrates a computer generated graphic as would be seen on the display screen of FIG. 1, which includes display of a turnover time clock showing a time interval starting with when the last patient left the operating room.

Upon completion of the procedure, when the operation has ended and the patient exits the operating room the "patient out" status is entered in the computer for documenting in the patient's EMR by the circulating nurse, and the Pelorus system changes the display to show a green turnover time clock that begins. This is represented in FIG. 9.

Figure 10:
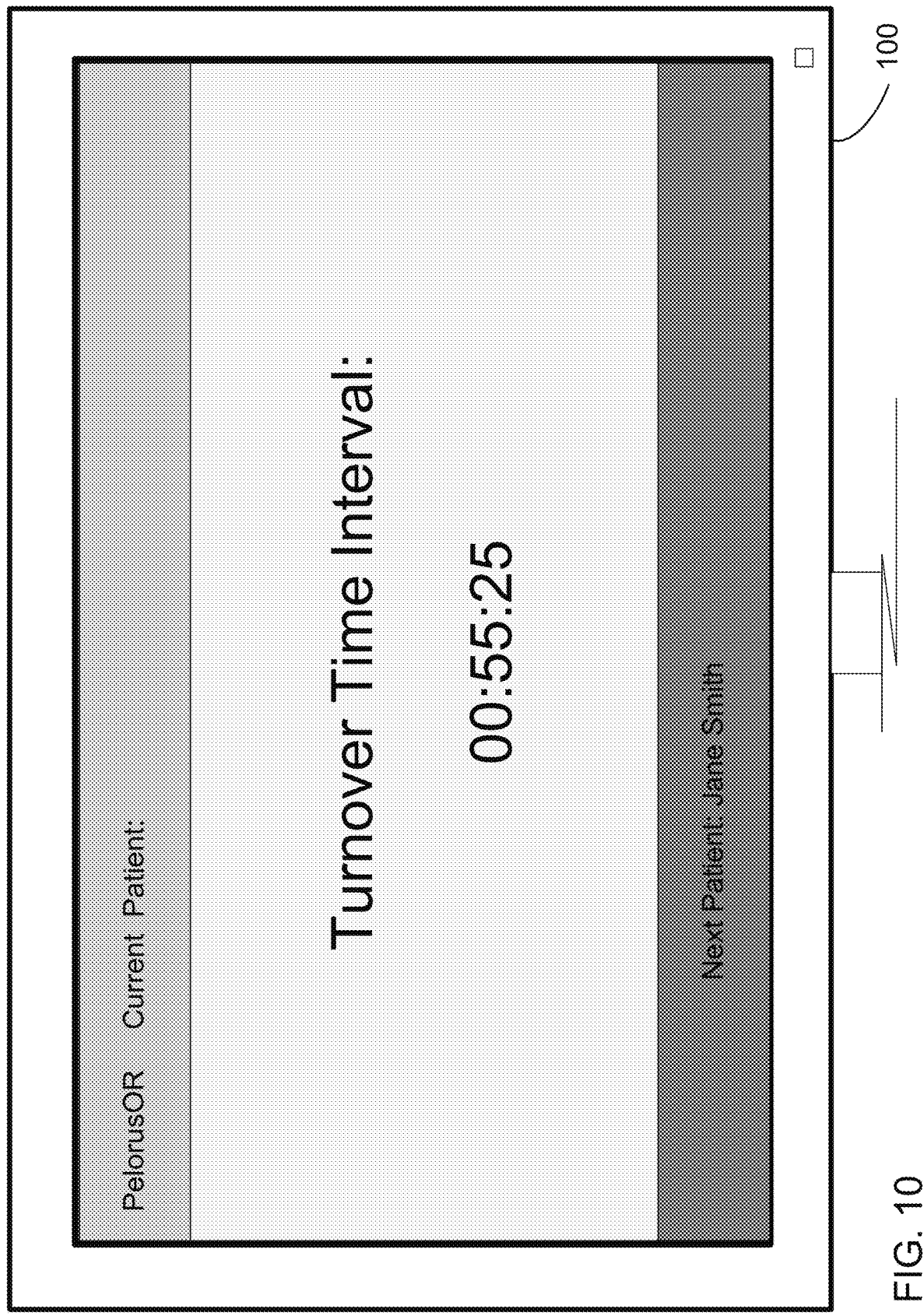
FIG. 10 illustrates a computer generated graphic as would be seen on the display screen of FIG. 1, which includes display of an indication that a turnover time interval is close to being longer than acceptable.
Figure 11:
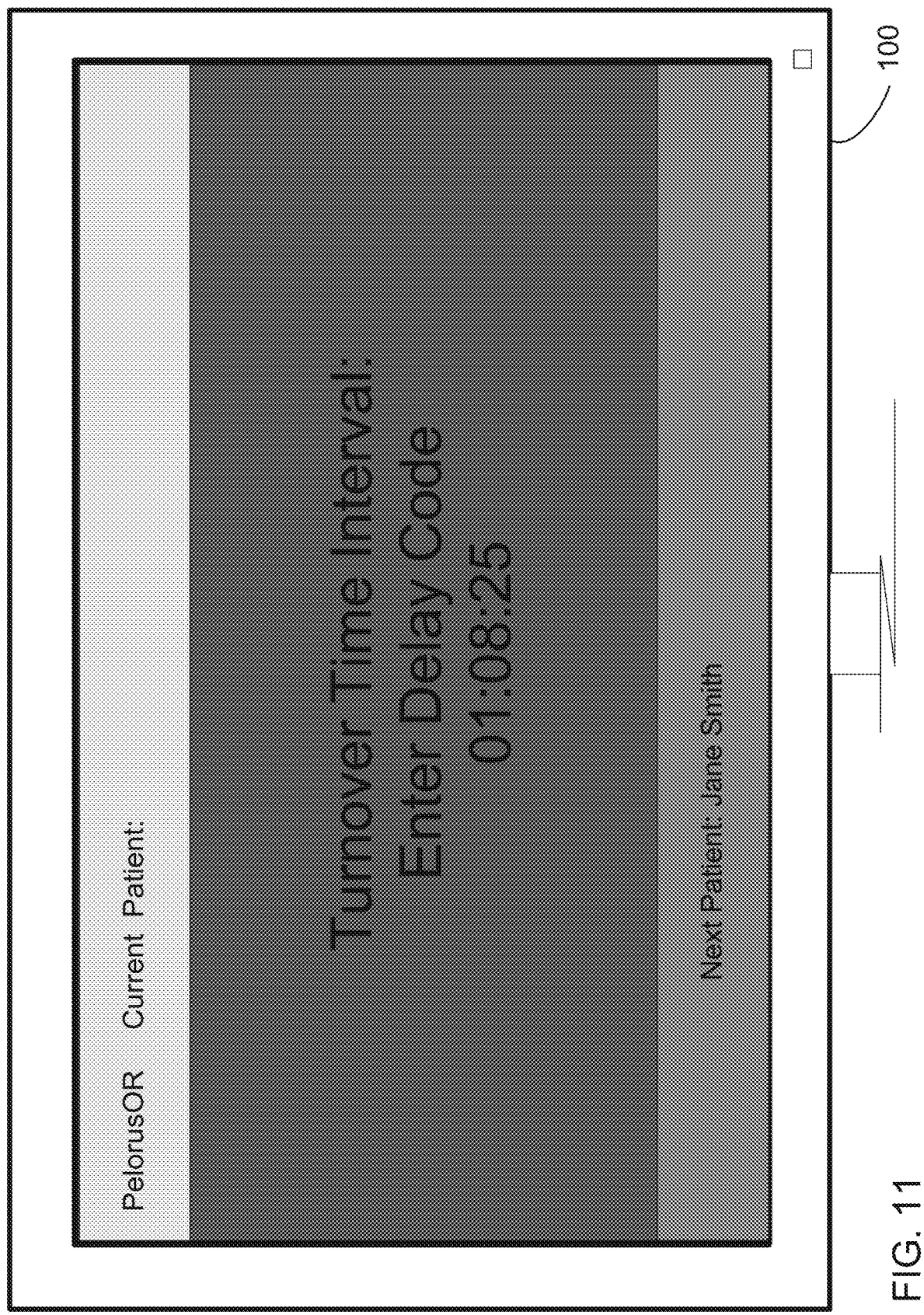
FIG. 11 illustrates a computer generated graphic as would be seen on the display screen of FIG. 1, which includes display of an indication that a turnover time interval has become longer than acceptable.

Preferably, a yellow color-coded clock is shown if the turnover time approaches a predetermined length of time deemed to be unacceptable, such as for example, an hour. This is represented in FIG. 10. A red color-coded clock is shown if the turnover time exceeds the predetermined length of time deemed to be unacceptable, as seen in FIG. 11. In this regard, the clock turns yellow as a warning that the clock is about to turn red. Furthermore, the display preferably prompts for the entry of a delay code once this predetermined length of time is exceeded, as seen in FIG. 11. It further will be appreciated that the "Turnover Time" here is defined to begin at the time when one patient leaves the operating room and lasts until the next patient enters the operating room.

Figure 12:
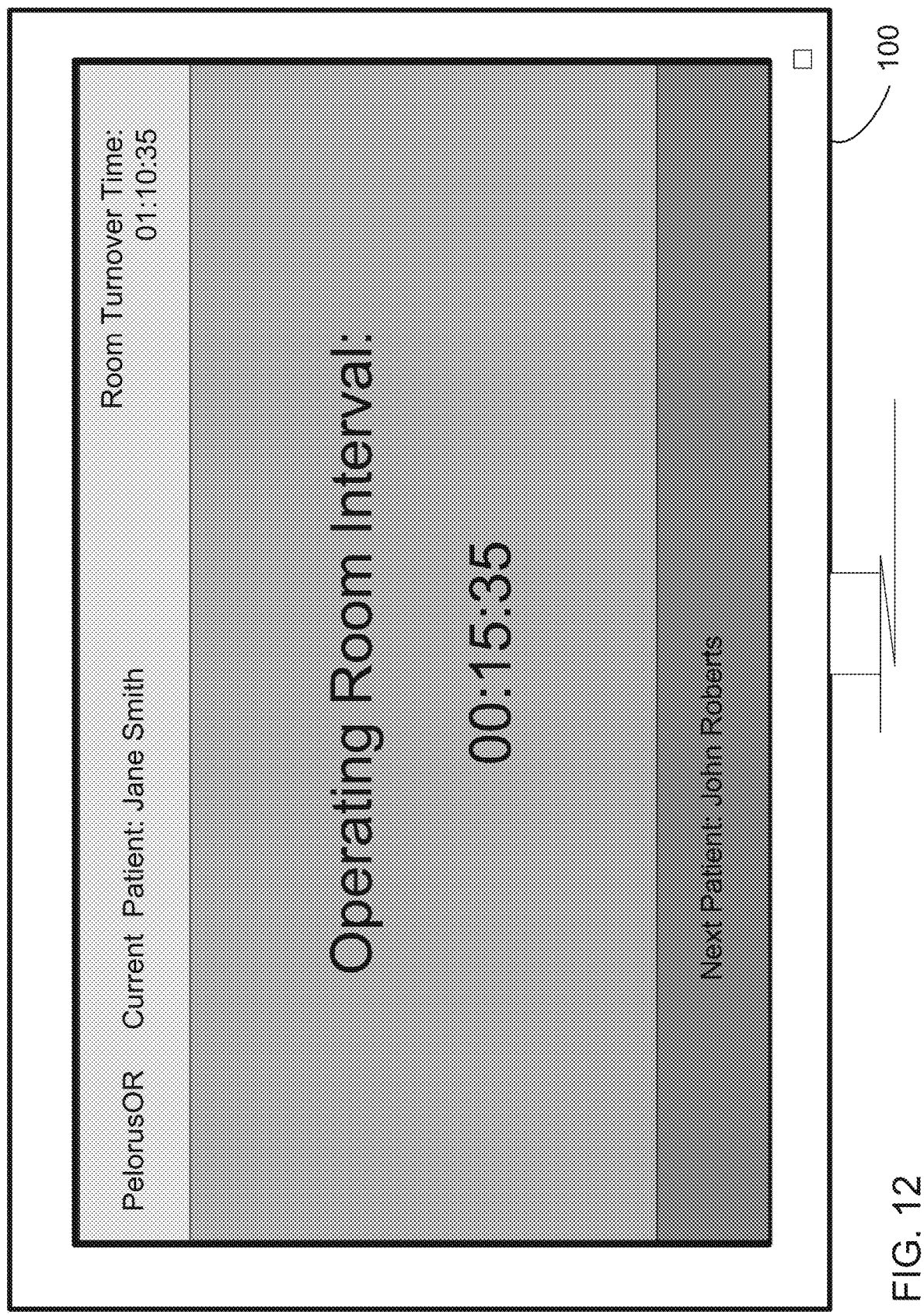
FIG. 12 illustrates a computer generated graphic as would be seen on the display screen of FIG. 1, which includes display of an indication of an operating room interval time clock that has begun for a subsequent scheduled case.

Subsequently, when the next patient is documented as in the operating room, the display again turns green and a procedure clock begins to run, as seen in FIG. 12. Moreover, the last room turnover time may be displayed, too, and preferably is displayed throughout the operation making it immediately available for the surgeon to review.

Figure 13:
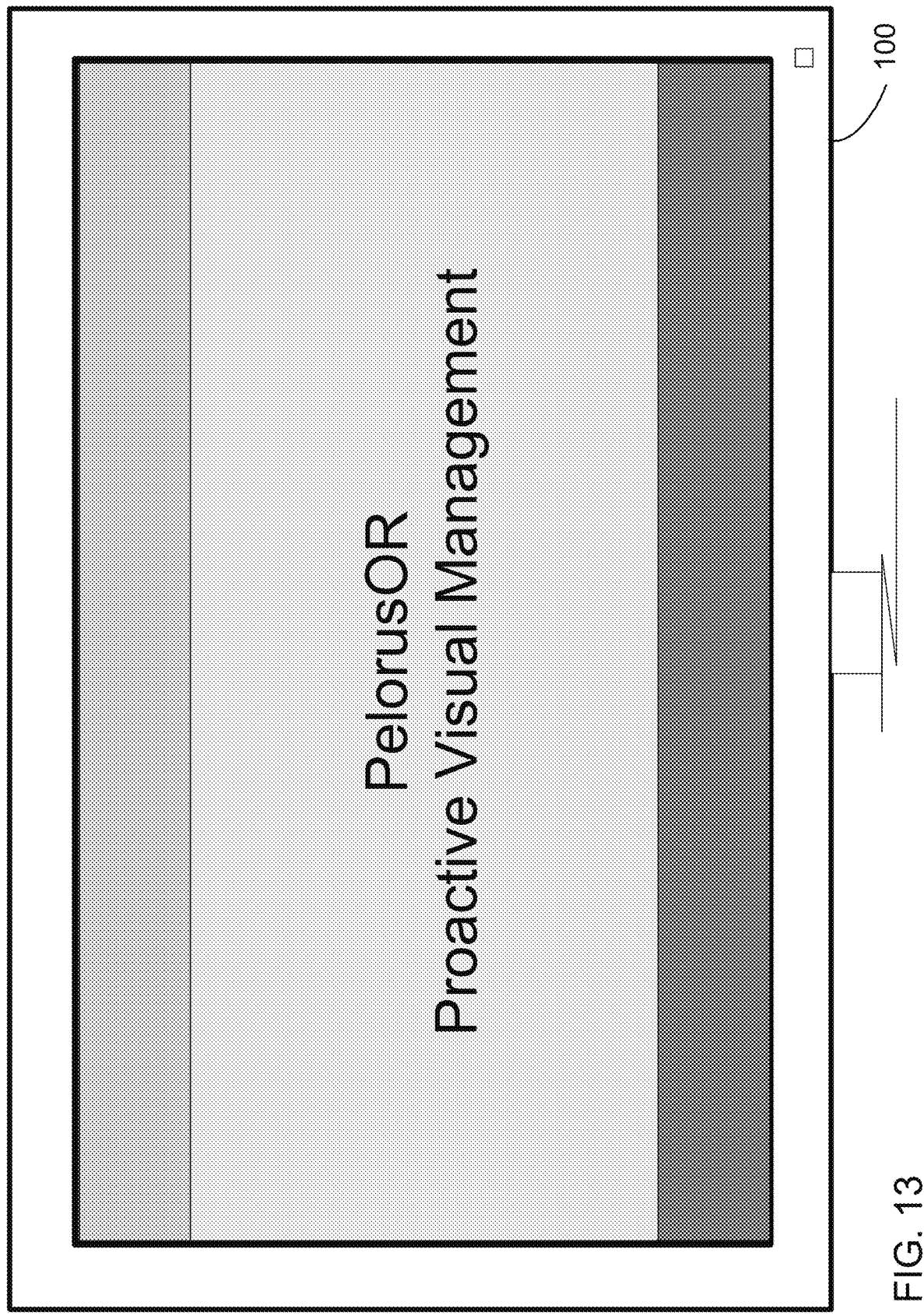
FIG. 13 illustrates a computer generated graphic as would be seen on the display screen of FIG. 1, which includes display of an indication that there are no further scheduled cases in the particular operating room for the day, i.e., that the end of the day has been reached.

Following a procedure and recording of the "patient out" status in the patient's EMR, if no subsequent procedure is scheduled in the operating room, then the display turns light blue as seen in FIG. 13, thereby indicating the end of the day.

Figure 14:
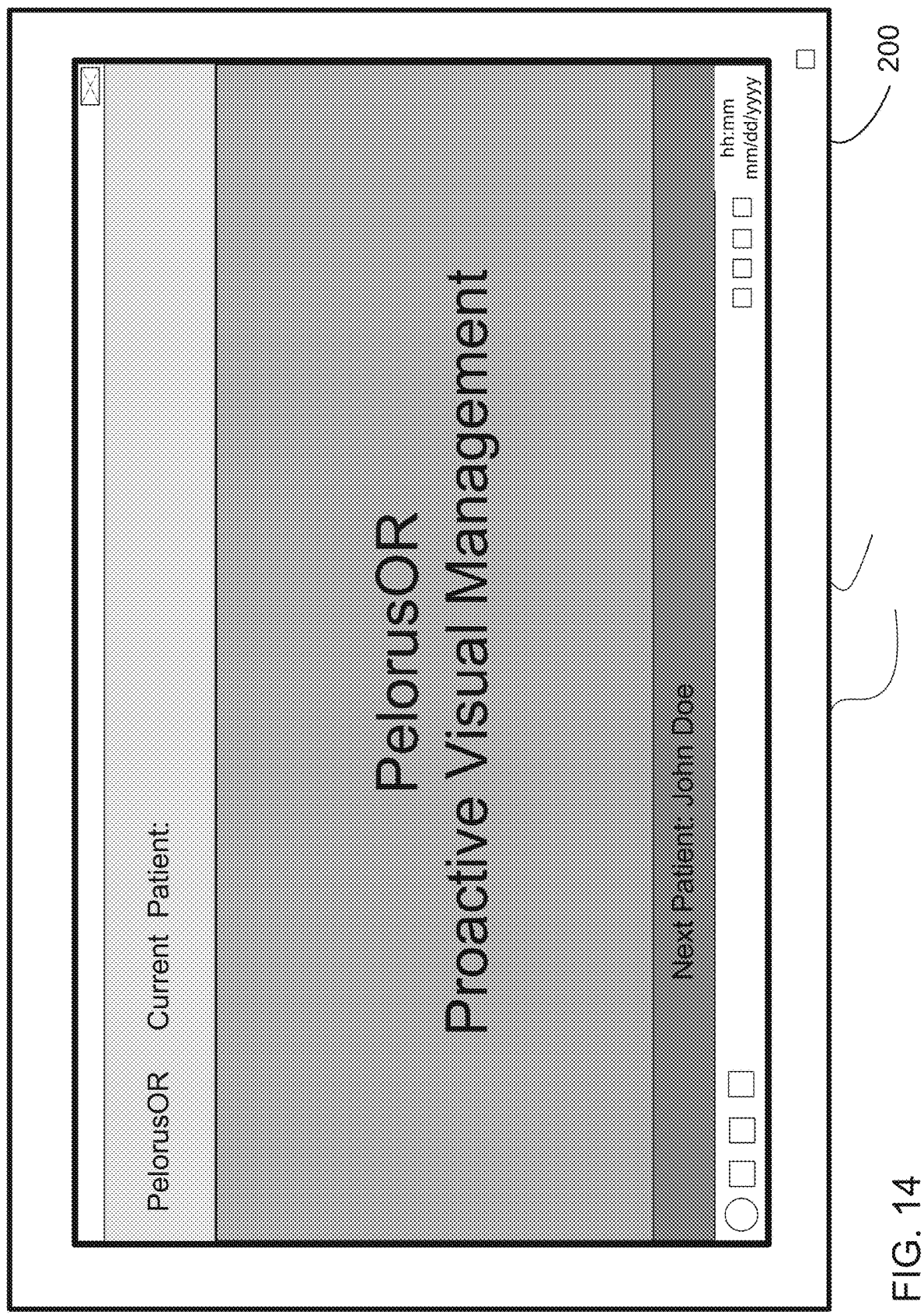
FIGS. 14-15 correspond to FIGS. 1-2 in the context of the implementation of a preferred embodiment on a computer running a Microsoft Windows or Apple OS X operating system, in accordance with one or more aspects and features of a preferred embodiment.
Figure 15:
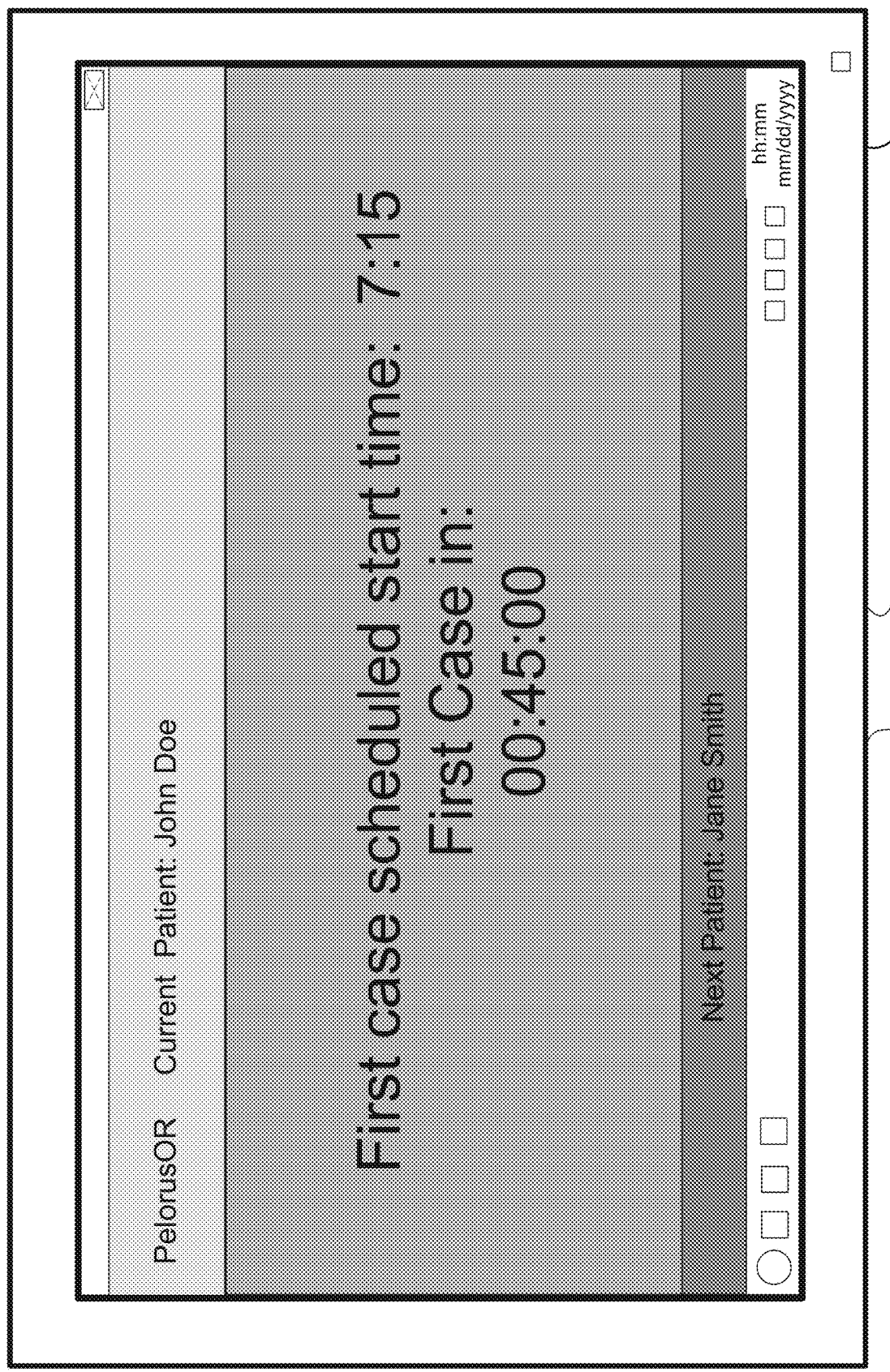

It will further be appreciated that the display of FIGS. 1-13 is illustrated as a self-standing computer monitor display 100, or television, wherein the generated graphics are shown in full screen. Alternatively, the above described screens may be shown on wall-mounted computer display 200 within an application window, such as those commonly found in the Microsoft Windows or Apple OS X operating systems. FIGS. 14-15 correspond to FIGS. 1 and 2 and are representative of such implementations, wherein the application window is seen as maximized.

Figure 16:
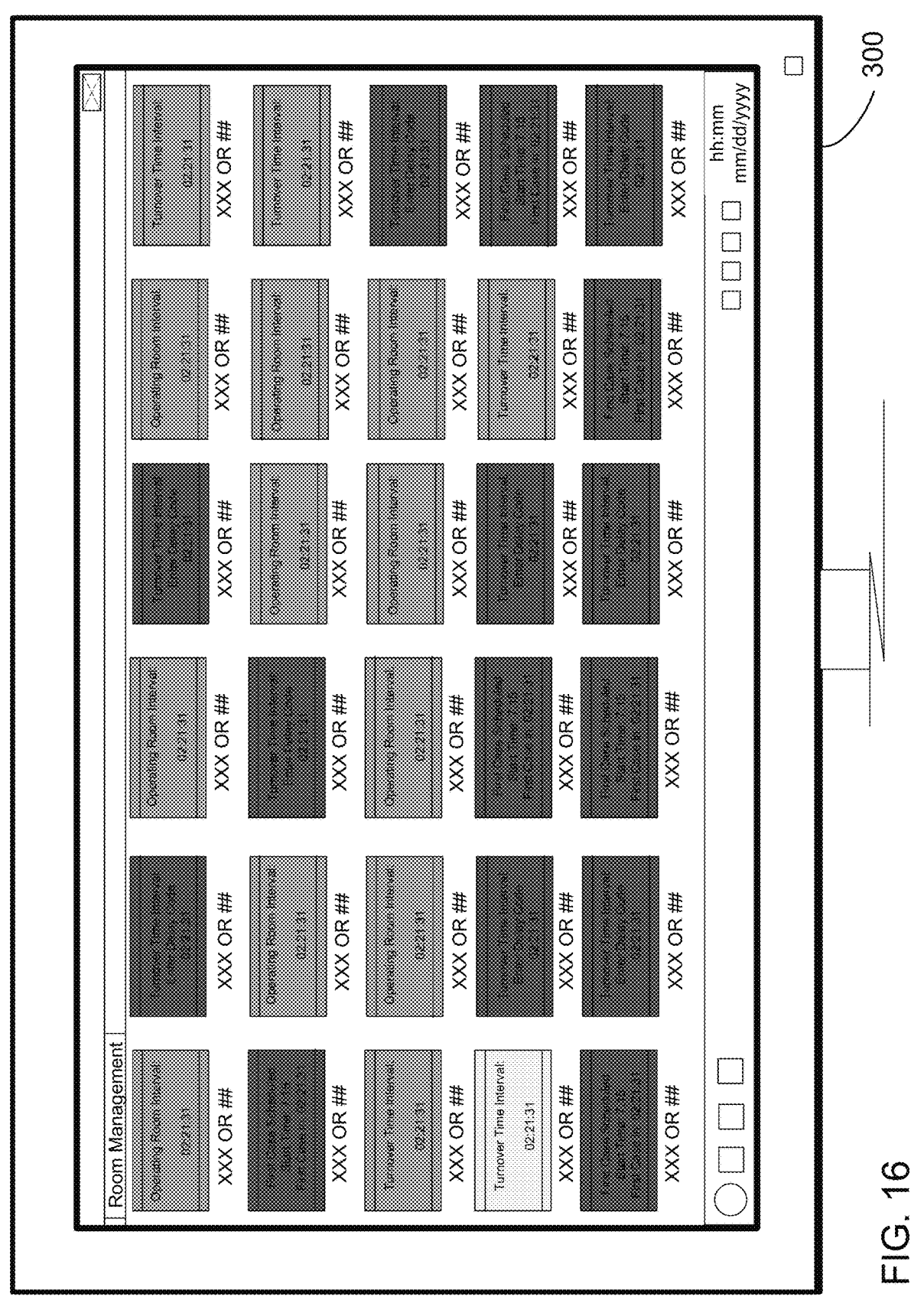

An exemplary operating room summary screen is shown in FIG. 16 and is illustrated on a computer monitor display 300 that may be located outside of the operating rooms. The screen preferably shows, or represents, the then currently displayed generated graphics as seen within each operating room, including those described above. In this respect, such utilization screens reveal a mini-display of what is being seen in each operating room and show, in a simple manner within the bounds of what can be seen, utilization information for all of the operating rooms.

Figure 17:
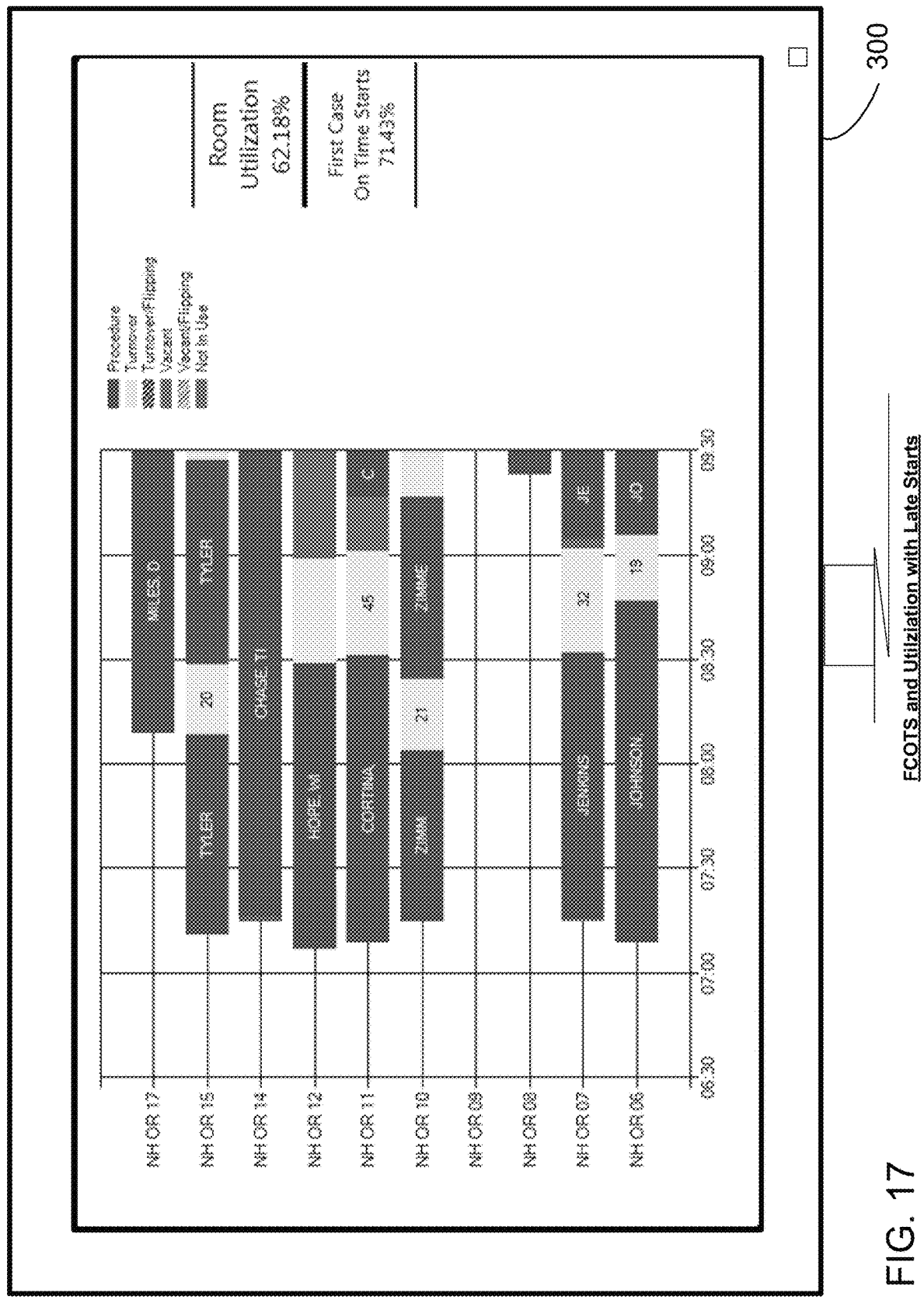
FIG. 17 illustrates a computer generated graphic as would be seen on the display screen of FIG. 16, which includes display of another utilization screen for operating rooms.

Another utilization screen is shown in FIG. 17. It prominently displays to healthcare providers in a surgeon lounge, for example, critical efficiency management data for the entire operating rooms, including real time room utilization and percentage of on time starts. There is a minute-to-minute room utilization calculation as well as real time "First Case On Time Starts" data that is displayed for the entire day. This is another example for showing and comparing different rooms and gives an overall view of how the day is progressing. In this screenshot there is no flipping amongst the rooms shown (no hash pattern, as described below). Also, this set of room shows late starts in NH OR 14 and NH OR 07. This is drawn as red (inefficient) time from the target start time (7:15 AM in this case) and the actual room "in" time for the first case in the room.

Figure 18:
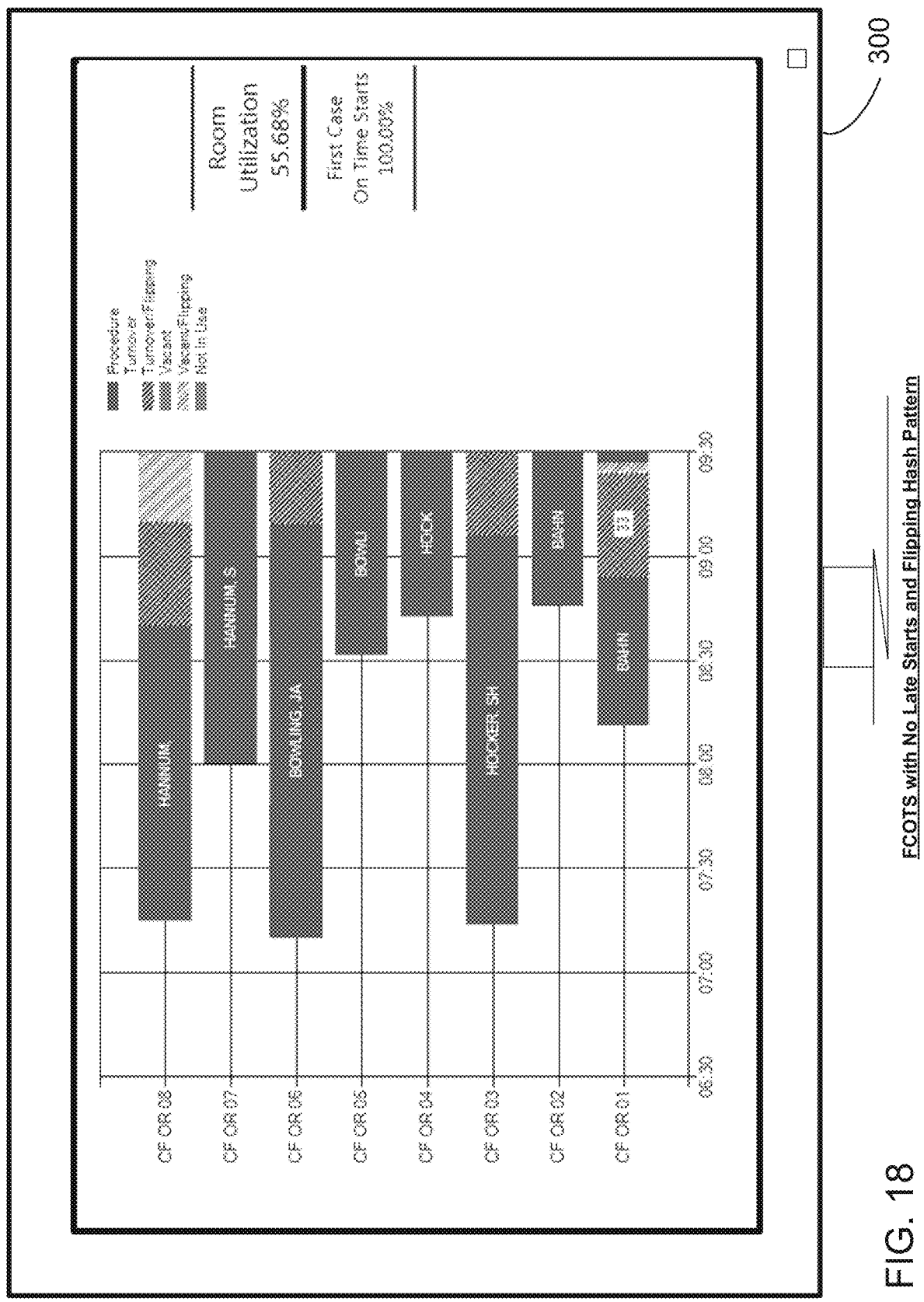
FIG. 18 illustrates a computer generated graphic as would be seen on the display screen of FIG. 16, which includes display of another utilization screen similar to that seen in FIG. 17.

A similar utilization screen is shown in FIG. 18. Furthermore, as seen therein, hashed patterns or other visual indicators of the utilization screen GUIs can be displayed that demonstrate when the same surgeon is concurrently using two rooms, "flipping" between them with acceptable downtimes. For example, when a surgeon is flipping between rooms a hashed pattern can be shown as covering the well-used yellow and red turnover time bars in the second room softening them as acceptable use of the operating room.

Further in this regard, it will be appreciated that "flipping" is an operating room scheduling technique used to minimize the downtime for the surgeon between procedures, and comprises using two operating rooms alternatively with the surgeon moving directly from the close on one case to the start of the next, thereby minimizing physician turnover time. In FIG. 18, flipping is shown as occurring in CF OR 03/04 (Surgeon=HOCKER), CF OR 05/06 (Surgeon=BOWLING), CF OR 07/08 (Surgeon=HANNUM). While downtime in the operating room between cases is inefficient time, it is planned efficiently and so should be viewed less critically when assessing operating room performance. The Pelorus system denotes this by providing color coding (hashing) of Turnover Time and Vacant Time during flipping. This is determined by looking across all other operating rooms at the end of a case and determining if the surgeon for the completed case has an active case in another room at the same time. Since flipping introduces some inefficiency in exchange for the benefit of keeping the surgeon busy so more cases are done per unit of surgeon time at the hospital, there also is the concept to good flipping and bad flipping. A good flip is defined as operating room downtime (turnover or vacant) where there is an active case in another room for the duration of that time. A bad flip is defined as a case where a procedure is occurring in another room but the active procedure time does not fully overlap the turnover or vacant time. The hashed bars are used for good flips and solid bars are used for bad flips. Also, the surgeon's name is on each procedure bar, which provides another indication that flipping is occurring in the pair of rooms.

Every minute counts in the expensive arena of the operating room. It is thought that the Pelorus system will assist in achieving on time starts and decreasing prolonged turnovers. When used properly, scheduling strategies can be deployed that will decrease downtime allowing for either more time to operate or an earlier end to the workday. While medicine is certainly not a timed event, there are aspects of improving time management in every hospital.

If a hospital already has an EMR for its operating rooms, the Pelorus systems preferably easily interfaces to it, allowing OR efficiency to be maximized.

The components of the Pelorus system in accordance with one or more aspects and features of the invention include computer-networked modules comprising: a data collector module; a display manager module; and a display module.

The data collector module is executed on a server in a data center and interfaces with the infrastructure of the networked healthcare facility/healthcare computer system. The display manager module also is executed on a server in the data center. The data center and/or server may be owned, operated, and/or maintained by a third-party service provider of the Pelorus system, and may be remotely located relative to the healthcare facility/healthcare system. The data collector module collects information from one or more other systems in the networked healthcare facility/healthcare computer system, and populates a database with the collected information. For example, the database preferably is a SQL database; the data collector module preferably integrates with EMR software such as that provided by EPIC; and an HL7 feed preferably is used as the interface between the data collector module and the networked healthcare facility/healthcare computer system (e.g., one or more hospitals). Such communication preferably is one-way to the server and may include secure communications over the Internet. Alternatively, the server may be located on the premises of the healthcare facility/healthcare system and further may be owned, operated and controlled by the healthcare facility/healthcare system in at least some implementations.

The display manager module provides an analysis engine that analyzes the data in the database populated by the data collector module; generates data for display by the display module; and provides the data feed to each display module for the displaying data.

Each display in the Pelorus system is driven by a display module that is executed on a computer attached to the display. The display module obtains information from the display manager module and drives the display with formatted information. The displays themselves preferably comprise large (46-inch) displays positioned in each OR and in key visible locations throughout the employee-only areas of the healthcare facility/healthcare system.

Preferably, the Pelorus system is setup to display on one or more screens a number of clinical documentation challenges for tracking as part of the Surgical Care Improvement Project (SCIP) like, for example, antibiotic dosing and other relevant clinical information.

Utilization summary screens positioned throughout the healthcare facility/healthcare system show real time OR utilization across the board for an entire OR network, including the percentage of "First Case On Time Starts" (FCOTS), real time OR utilization, and surgeon arrival times. It is further contemplated that personnel productivity also be shown.

In will be better appreciated form the foregoing that preferred metrics addressed by the Pelorus system include: First Case On Time Starts (FCOTS); Room Turnover Time Interval (RTOT); Operating Room Time Interval; Room Utilization; and SCIP Data Points, all as now discussed below.

First Case on Time Starts (FCOTS)

Successful FCOTS is defined by the Pelorus system as the time the first patient is scheduled to arrive in the OR and the actual time documented as "Patient in Room" by the circulating nurse before or at the scheduled time. Expressed as a percentage, this measures the percent of cases scheduled to start at a specified time or within a specified window of time that did, in fact, start at or before such specified time. Based on scheduling information and the first "Patient in Room" event of the day for the OR rooms, FCOTS is calculated. Only rooms with first starts at the specified time or within the specified range of start times are considers for the total count of cases for the calculation. All cases that start at or before the scheduled start time are considered a First Case On Time Start (FCOTS). The national average for FCOTS remains around 60% with the top 5% of hospitals achieving a 90% rating. A typical OR will have an annual range from 35-85% FCOTS. The problems with not starting an OR case on time relate to the arrival time of the surgeon, timely movement from the OR staff, patient issues, and equipment issues.

The Pelorus system starts a green countdown clock 45 minutes prior to the scheduled first case. If the patient is not in the room 5 minutes early, a warning screen turns red. If the patient is not in the operating room on time, a message instructs the OR circulating nurse to "Enter a Delay Code" into the computer. Historically, there are wide variations in delay code data entry making these reports of limited benefit. If a delay is documented and if desired by the user, the delay code remains on the screen for the duration of the operation. Through this method, the Pelorus system standardizes and validates publicly what actually is a delayed case and the cause of the delay.

The Pelorus system also includes a surgeon sign-in touch pad which should be positioned in the preoperative area. After a surgeon has evaluated their first patient and is ready for the patient to be taken to the operating room, the surgeon pushes a single button which sends a message to the screen in the operating room and documents the "Surgeon Ready" time. If desired by the user, this time remains on the OR screen throughout the first operation. Surgeon ready times can be tracked and utilized for operating room time availability. For example, chronically late surgeons may lose their future opportunity to start at the beginning of the day or late surgeons will not be given a second room to flip their case into, which may cost them hours of efficient operating time.

Room Turnover Time Interval (RTOT)

RTOT is defined as the time interval from when the last patient left the OR to the time the next patient enters the OR, as documented by the circulating nurse in the EMR. RTOT remains a source of continued debate throughout the operating room and in administrative meetings. OR time is estimated at $1,000-$1,200 per hour and issues of patients waiting for critical surgery, staff overtime expenses, and surgeon inconvenience make this issue foremost in the minds of all involved parties. After a surgeon leaves the room, an assistant will often close the wound, the nurses bandage the wound, and the patient must be awakened from anesthesia and be transported to the recovery room or post anesthesia care unit (PACU). The OR is then thoroughly cleaned and sterile instrumentation is setup for the next operation. The next patient then enters the room and is anesthetized. This process may take up to 90 minutes between large operations and leaves surgeons frustrated on a daily basis. The perception of long RTOT is often not close to the reality of this time interval and RTOT remains the focus of most throughput discussions.

The reality of RTOT is that it varies by operation and facility type. Large tertiary medical centers turn a room in 35 minutes for big operations, community hospitals turn a room in 30 minutes, and ambulatory centers turn a room in 20 minutes or less. The 90-minute time interval that a surgeon waits often gets confused with the RTOT and frustration mounts.

The display screens of the Pelorus system are green as a patient exits the operating room and the "Turnover Time Interval" clock begins running. If the next patient is not in the room within five minutes of the preset goal, a warning screen is displayed in red. For example, in a community based facility with a RTOT goal of 30 minutes, the screen turns red at 25 minutes. As the 30-minute time interval passes, a message to "Enter a Delay Code" is generated, again standardizing the delay code report.

Once the next patient has entered the OR, the "Operating Room Time Interval" clock begins and the Delay Code and last RTOT are left on the screen at the user's discretion. The reality of real time tracking brings everyone into an equally accountable equation. Typically, a surgeon will re-enter the OR to an elapsed procedure time of about 20 minutes quickly understanding that the staff has been waiting on them. Interested surgeons soon change their practice pattern to be waiting in the OR as the patient arrives saving valuable minutes.

Operating Room Time Interval

The potential power of the "Operating Room Time Interval" will need to delicately distributed. Standard operations like joint replacement have a wide variation in surgeon time with some surgeons completing a total knee replacement in under 50 minutes while others take over 4 hours on average. Public display of surgeon operating times for other surgeons to see will change practice patterns and will likely lead to better utilized ORs.

Room Utilization

Room utilization is calculated across a set of OR rooms as total procedure times divided by total room time since the first case start times for the day.

SCIP Data Points

The Surgical Care Improvement Project (SCIP) is a Centers for Medicare and Medicaid Services (CMS) dictated quality improvement project that determines government reimbursement rates and penalties for hospitals and physicians based on purported quality metrics. Every few years the CMS determines the clinical metrics to be tracked and hospitals spend a huge amount of effort trying to avoid penalties. It is common for large hospitals to be annually penalized millions of dollars for missing quality marks for antibiotic timing, readmission rates, etc.

Figure 19:
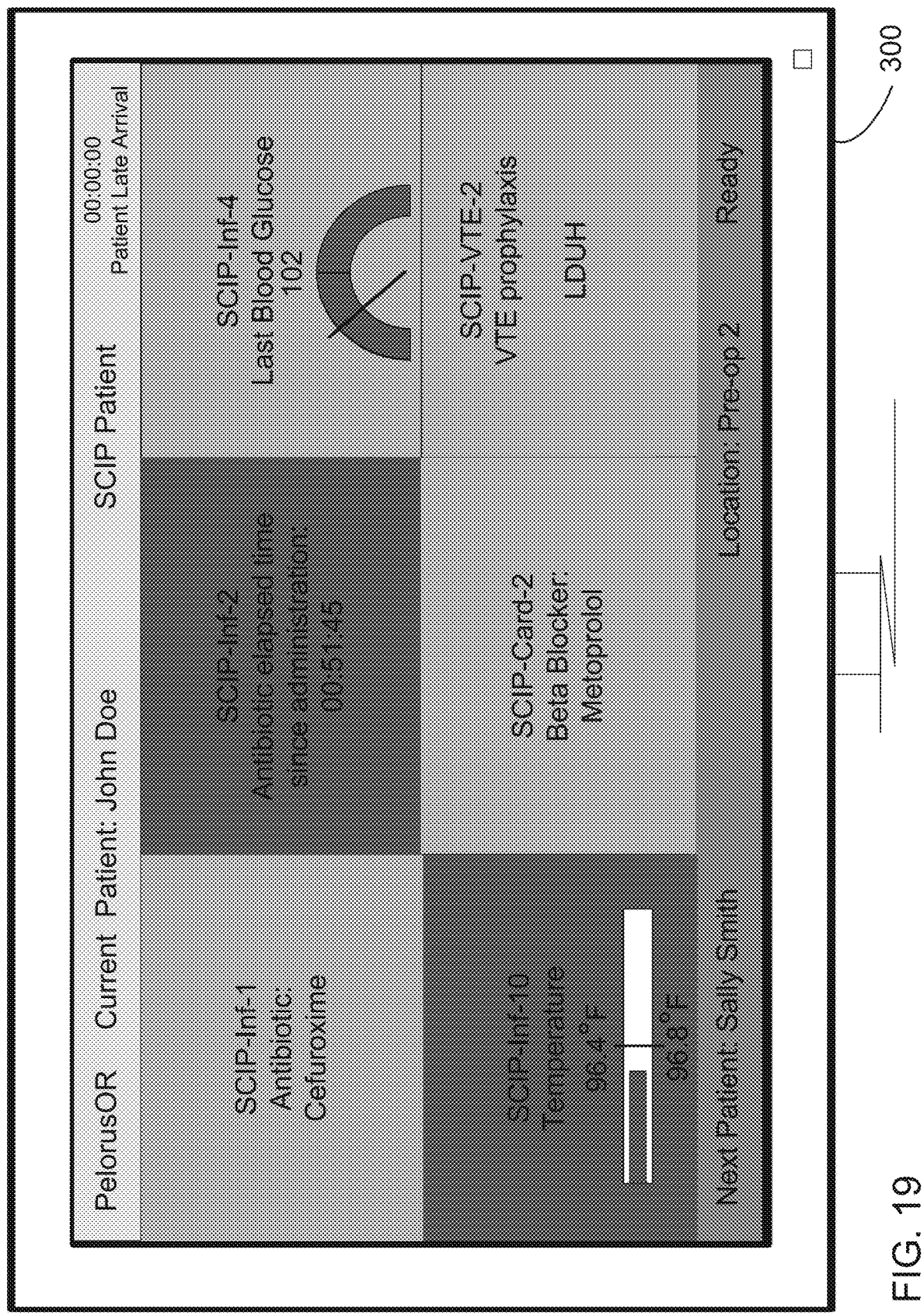
FIG. 19 illustrates a computer generated graphic as would be seen on a display screen, which includes display of clinical information and SCIP information, in accordance with one or more aspects and features of a preferred embodiment.

One example of an elusive operating room SCIP requirement is antibiotic choice and timing. CMS requires that the correct antibiotic be delivered to a patient within a one-hour to two-hour interval prior to incision. The Pelorus system has the potential capability to determine if the correct antibiotic has been chosen and to start an antibiotic clock in a red color running until the incision is documented. If the incision occurs within the required timing parameter, the box turns green and the clock stops. The potential of real time visual management with SCIP data is believed to be very interesting to hospital administrators and offer a quick return on investment. An exemplary display screen with clinical information/SCIP information is shown in FIG. 19.

In addition to the foregoing, and with reference to the Appendix, FIGS. 25 and 26 of the Appendix show a prototype of a portable apparatus for use in an operating room including a tablet (in the form of an iPad) for data entry, in accordance with one or more aspects and features of the invention; and, FIG. 27 of the Appendix shows a surgeon lounge including a wall-mounted display screen located outside of the operating rooms, in accordance with one or more aspects and features of the invention. Other areas may include, for example, a staff lounge and an OR front desk.

An important preferred feature of the Pelorus system is the truth in real time data. Everyone sees it and everyone believes it. Problems and inaccuracies can be immediately addressed. This is different than discussing the OR efficiency metrics at a quarterly meeting or correcting inaccurate SCIP data after the fact.

Problems addressed by the Pelorus system relate to OR inefficiencies, including: (1) OR downtime and financial loss; (2) surgeon waiting times; (3) inaccurate delay code data; (4) poorly documented clinical data and SCIP penalties; (5) staff overtime; and (6) lengthy exposure to anesthesia.

Advantages of the Pelorus system relate to visual management, and include: (1) accountability of all personnel; (2) successful SCIP compliance; and (3) improvement in performance due to public display of the data (sometimes referred to as the "Hawthorne Effect").

Lastly, it will be appreciated that all network operating rooms preferably are visible. Physicians, nurses, IT staff, and administrators can readily see operational status of all ORs in real time and for the entire day as it is progressing.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. An apparatus for improving operating room throughput for a plurality of operating rooms, comprising:
    (a) a networked data collector module comprising a networked electronic device having a processor and computer-executable instructions by which the networked data collector module is configured to receive data in real-time indicating a patient's arrival in an operating room and the patient's departure from the operating room and, based thereon, populate data in a database;
    (b) a networked display manager module comprising a networked electronic device having a processor and computer-executable instructions by which the networked display manager module is configured to analyze data in the database populated by the data collector module and calculate data for display including real-time first case on time start (FCOTS) metrics, real-time operating room utilization metrics, and operating room turnover time metrics; and
    (c) a plurality of networked display modules, each networked display module comprising a networked electronic device having a processor and computer-executable instructions by which the networked display module is configured to receive and display data calculated by the networked display manager module including at least one of the real-time FCOTS metrics, the real-time operating room utilization metrics, and the operating room turnover time metrics.

2. The apparatus of claim 1, wherein the networked electronic device further comprises a networked electronic device having a processor.

3. A system for improving operating room throughput for a plurality of operating rooms, comprising:
    (a) a networked data collector module comprising a networked electronic device having a processor and computer-executable instructions by which the networked data collector module is configured to receive data indicating a patient's arrival in an operating room and the patient's departure from the operating room and, based thereon, populate data in a database;
    (b) a networked display manager module comprising a networked electronic device having a processor and computer-executable instructions by which the networked display manager module is configured to analyze data in the database populated by the data collector module and calculate data for display including real-time first case on time start (FCOTS) metrics, real-time operating room utilization metrics, and operating room turnover time metrics; and
    (c) a plurality of networked display modules, each networked display module comprising a networked electronic device having a processor and computer-executable instructions by which the networked display module is configured to receive and display data calculated by the networked display manager module including at least one of the real-time FCOTS metrics, the real-time operating room utilization metrics, and the operating room turnover time metrics;
    (d) wherein each of the plurality of operating rooms has located therein a display by which operating room personnel may view a display generated by one of the plurality of networked display modules, the display including at least one of the real-time FCOTS metrics, the real-time operating room utilization metrics, and the operating room turnover time metrics.

4. The system of claim 3, wherein the FCOTS metrics are expressed as percentages representing the number of cases scheduled to start in the operating rooms at a specified time or within a specified window of time that did, in fact, start at or before such specified time.

5. The system of claim 3, wherein the database includes scheduling information for each of the plurality of operating rooms for calculating the FCOTS metrics.

6. The system of claim 3, wherein the networked display module is further configured to display color-coded time clocks identifying delayed operating room start times and unacceptable operating room turnover times.

7. The system of claim 3, wherein the networked data collector module receives data relating to clinical metrics and populates the database based thereon, and wherein the networked display module is further configured to display data from the database relating to the clinical metrics.

8. The system of claim 7, wherein the data relating to the clinical metrics comprises data regarding antibiotics; antibiotic timing or antibiotic dosing; patient temperature; patient blood glucose level; and beta blockers.

9. The system of claim 3, wherein the networked electronic device of the networked data collector module comprises a server that communicates with a computer network of a healthcare facility.

10. The system of claim 9, wherein an HL7 feed is used to communicate between the data collector module and the computer network of the healthcare facility.

11. The system of claim 9, wherein the communication comprises a one-way data feed from the computer network of the healthcare facility to the server.

12. The system of claim 9, wherein the data collector module obtains data from electronic medical record (EMR) software of the computer network of the healthcare facility.

13. The system of claim 12, wherein the data that is obtained is EMR data already being recorded for a patient for other purposes, whereby the system leverages the patient EMR data for an additional purpose.

14. The system of claim 3, wherein the networked display manager module is configured to provide a data feed of the calculated data for receipt by the plurality of networked display modules.

15. The system of claim 3, wherein the system further comprises a surgeon sign-in module comprising a networked electronic device having a processor and computer-executable instructions by which the surgeon sign-in module is configured to receive user input indicating that a surgeon is ready to begin a case of that surgeon in a specific operating room.

16. The system of claim 15, wherein the networked electronic device comprises a tablet computer located in a preoperative area of a healthcare facility.

17. The system of claim 15, wherein the networked electronic device communicates data indicative that the surgeon is ready for storing in the database populated by the networked data collector module; wherein the networked display manager module is further configured to provide data indicative that the surgeon is ready to a networked display module for display in the specific operating room; wherein a networked display module is further configured to display indicators that demonstrate when a surgeon is concurrently using two operating rooms; and, wherein a networked display module is further configured to display indicators that demonstrate when a surgeon is concurrently using two operating rooms with acceptable downtimes.

* * * * *